United States Patent [19]
Lopez et al.

[11] Patent Number: 5,972,656
[45] Date of Patent: Oct. 26, 1999

[54] MERCURY BINDING POLYPEPTIDES AND NUCLEOTIDES CODING THEREFORE

[75] Inventors: Osvaldo Lopez; Dwane E. Wylie, both of Lincoln; Fred W. Wagner, Walton, all of Nebr.

[73] Assignee: BioNebraska, Inc., Lincoln, Nebr.

[21] Appl. No.: 08/888,366

[22] Filed: Jul. 3, 1997

Related U.S. Application Data

[63] Continuation of application No. 08/187,407, Jan. 27, 1994, abandoned, which is a continuation-in-part of application No. 07/990,542, Dec. 14, 1992, Pat. No. 5,503,987, which is a continuation of application No. 07/493,299, Mar. 14, 1990, abandoned, which is a continuation-in-part of application No. 07/324,392, Mar. 14, 1989, abandoned.

[51] Int. Cl.$^6$ .......................... G01N 33/53; C12P 21/04; C07K 16/00; C07K 16/44

[52] U.S. Cl. .......................... 435/69.3; 435/7.1; 435/7.92; 435/240.27; 514/12; 514/13; 514/14; 514/15; 514/16; 514/17; 514/18; 424/141.1; 530/388.1; 530/387.1; 530/388.9; 530/389.9

[58] Field of Search ................................. 435/7.92, 69.3, 435/240.27, 7.1; 514/12, 13, 14, 15, 16, 17, 18; 424/141.1; 530/388.1, 387.1, 388.9, 389.9

[56] References Cited

U.S. PATENT DOCUMENTS

| | | |
|---|---|---|
| 4,078,049 | 3/1978 | Feliz et al. . |
| 4,281,065 | 7/1981 | Lin et al. . |
| 4,454,106 | 6/1984 | Gansow et al. . |
| 4,456,691 | 6/1984 | Stark . |
| 4,472,509 | 9/1984 | Gansow et al. . |
| 4,474,893 | 10/1984 | Reading . |
| 4,530,786 | 7/1985 | Dunbar et al. . |
| 4,608,337 | 8/1986 | Croce . |
| 4,668,771 | 5/1987 | Kawakami et al. . |
| 4,677,070 | 6/1987 | Larrick et al. . |
| 4,681,782 | 7/1987 | Ozkan . |
| 4,701,408 | 10/1987 | Koestler . |
| 4,731,238 | 3/1988 | Neville et al. . |
| 4,760,155 | 7/1988 | Heffernan et al. . |
| 4,760,156 | 7/1988 | Heffernan et al. . |
| 4,762,781 | 8/1988 | Ceffard . |
| 4,764,359 | 8/1988 | Lemelson . |
| 4,772,551 | 9/1988 | Hart et al. . |
| 4,772,892 | 9/1988 | Meares . |
| 4,778,752 | 10/1988 | Curtiss et al. . |
| 4,793,986 | 12/1988 | Serino et al. . |
| 4,797,473 | 1/1989 | Tarsio et al. . |
| 4,859,613 | 8/1989 | Lawrence . |
| 5,055,562 | 10/1991 | Koganty . |
| 5,112,606 | 5/1992 | Shiosaka et al. . |
| 5,112,738 | 5/1992 | Buckler et al. . |
| 5,354,652 | 10/1994 | Silbergeld . |
| 5,503,987 | 4/1996 | Wagner et al. .......................... 435/7.94 |
| 5,532,136 | 7/1996 | Carlson et al. .......................... 435/7.92 |
| 5,620,856 | 4/1997 | Carlson et al. .......................... 435/7.1 |
| 5,639,624 | 6/1997 | Wagner et al. .......................... 435/7.92 |
| 5,807,695 | 9/1998 | Wagner et al. .......................... 435/7.92 |

FOREIGN PATENT DOCUMENTS

| | | |
|---|---|---|
| 173 629 | 4/1986 | European Pat. Off. . |
| 0 235 457 A2 | 9/1987 | European Pat. Off. . |
| 286 232 | 10/1988 | European Pat. Off. . |
| 2 527 928 | 9/1983 | France . |
| WO 86/01407 | 3/1986 | WIPO . |
| WO 90/10709 | 9/1990 | WIPO . |
| WO 91/16912 | 11/1991 | WIPO . |
| WO 92/01781 | 2/1992 | WIPO . |
| WO 92/01939 | 2/1992 | WIPO . |

OTHER PUBLICATIONS

Advertisement for BiMelyze® Mercury Assay Kit published in the Mar./Apr. 1991 issue of Journal of Analytical Toxicology (vol. 15).
Advertisement for BiMelyze® Mercury Assay Kit published in the Sep. 1991 issue of Journal of the American Water Works Association (vol. 15).
Aviv et al., *Proc. Natl. Acad. Sci. USA*, 69, 1408 (1972).
Baker et al., *J. Biol. Chem.*, 253, 8444–8541 (1978).
Barbas et al., *Proc. Natl. Acad. Sci. USA*, 88, 7978 (1991).
Barbas et al., *Proc. Natl. Acad. Sci. USA*, 90, 6385 (1993).
Baum et al., *Chem. and Eng. News*, 19–20, (Jan. 23, 1989).
BiMelyze® Mercury Assay Kit sales brochure available to the public in Dec. 1990.
BiMelyze® Mercury Assay Protocol.
Bizollon et al., *Monoclonal Antibodfies and New Trends in Immunoassay*, Ch. A, 53–58 (1984).
Butler et al., *Advances in Immunol.*, 17, 255–310 (1973).
Caise, *Methods in Enzymology*, 92, (Academic Press, 1983) at 445–458.
Cenini, *Comp. BioChem. Physiol.*, 81C, 213–217 (1985).
Clarke et al., *J. Immunol. Methods*, 137, 65–72 (1991).
Cress et al., *ABL*, 16–19 (Feb., 1989).
Cwirla et al., *Proc. Natl. Acad. Sci. USA*, 87, 6378–6382 (1990).
DuVal et al., *Biochem. and Biophys. Res. Comm.*, 159(1): 177–184 (Feb. 28, 1989).
"EPA Industrial Toxics Project", BioNebraska, Inc. (Jan. 1991).

(List continued on next page.)

Primary Examiner—Frank C. Eisenschenk
Assistant Examiner—Mary K Zeman
Attorney, Agent, or Firm—Merchant & Gould P.C.

[57] ABSTRACT

Metal binding polypeptides which include an amino acid sequence coding for a variable region of a monoclonal antibody which immunoreacts with a mercury cation and nucleotides which include a nucleic acid sequence coding for the variable region are provided. The invention is also directed to fusion proteins which include a phage coat protein or portion thereof and the monoclonal antibody heavy chain variable region. The invention also provides bacteriophages which include the fusion protein in their coat. In addition, methods for detecting, removing, adding, or neutralizing mercuric cations in biological or inanimate systems through the use of the mercury binding polypeptides are provided.

22 Claims, 16 Drawing Sheets

OTHER PUBLICATIONS

Evans et al., *BioTechniques*, 8, 357 (1990).
Fasekas de St. Groth, *Immunological Methods*, I. Lefkovits and B. Pernis, editors; Academic Press (1979).
Forghieri et al., *Aust. J. Chem.*, 36, 1125–1132 (1983).
Friguet et al., *J. Immunol. Methods*, 77, 305–319 (1985).
Fuhr et al., *J. Am. Chem. Soc.*, 85, 6944 (1973).
Gigliotti et al., *J. Infect. Dis.*, 149, 43–47 (1982).
Gillespie et al., *Chemistry*, Allyn and Bacon Inc., 767–769 (1986).
Hainfeld, *Nature*, 333, 281–282 (1988).
Hawley's *Condensed Chemical Dictionary*; p. 748 (11th Edition).
Hohlfeld et al., *Monogr. Allergy*, 25, 50 (1988).
Horton et al., *Gene*, 77, 61–68 (1989).
Huse et al., *Science*, 246, 1275–1281 (1989).
*Immunology: The Science of Self–Nonself Discrimination*, Jan Klein, editor, John Wiley & Sons, NY, publisher; at p. 348 (1972).
Iverson et al., *Science*, 243, 1184–1188 (1989).
Kabakoff, *Enzyme Immunoassay*, Meggio, CT, ed., CVC Press, FL, 78–88 (1980).
Karin, *Cell*, 41, 9–10 (1985).
Kenmotsu, *Chem. Abstracts*, 13, 107669m (1984).
Klein, *Immunology: The Science of Self–Nonself Discrimination*, 348 (1982).
Kohler et al., *Nature*, 256, 495 (1975).
Kudsk, *Chem. Abstracts*, 82, 11898t (1973).
Langan et al., *J.A.D.A.*, 115, 867–880 (1987).
Lerner et al., *Sci. Amer.*, 258, 58–70 (1988).
Lerner et al., *T.I.B.S.* 12, (no page nos.) (1987).
Lewis et al., *J. Lab. Clin. Med.*, 88, 375–388 (1976).
Lindgarde et al., *Scand. J. Immunol.*, 3, 277–285 (1974).
Magos et al., *Chem. Abstracts*, 90, 98118a (1978).
Massey, *Nature*, 328, 457–458 (1987).
Masterson and Slowiriski, *Chemical Principals*, (W.B. Saunders, 1969).
Matsui et al., *J. Biol. Chem.*, 260, 4174–4179 (1985).
Meares, "Attaching Metal Ions to Antibodies," 339–352 (1987).
Meares, *Nucl. Med. Biol.*, 13, 311–318 (1986).
Merlini et al., *Clin. Exp. Immunol.*, 69, 148–156 (1987).
Mesna et al., *Comp. Biochem. Physiol.*, 99B, 181–185 (1991).
Naito, *Chem. Abstracts*, 95, 92911K (1980).
Napper et al., *Science*, 237, 1041–1043 (1987).
Ohara et al., *Nature*, 315, 333–336 (1985).
Parmley et al., *Gene*, 73, 305–318 (1988).
Patterson et al., *Am. Rev. Resp. Dis.*, 120, 1259–1267 (1979).
Pierce, *J. Occup. Med.*, 28, 589–592 (1986).
Pinekard, *Handbook in Exp. Immunology*, 3rd ed., Blackwell Scientific, publishers, 17.7–17.23 (1978).
Pollack et al., *Science*, 234, 1570–1573 (1986).
Reardan et al., *Nature*, 316, 265–268 (1985).
Reardan, *Dialog Information Services*, File 35: Dissertation Abstracts Online 1861 Jun. 90, Dialog accession No. 894111, vol. 46/07–B of Dissertation Abstracts International, p. 2326, (1985).
Roitt et al., *Immunology*, p. 5.8 (1989).
Rubenstein et al., *Nature*, 332, 426–429 (1988).
Sanger et al., *Proc. Natl. Acad. Sci. USA*, 74, 5463 (1977).
Sarkar et al. *Biotechniques*, 8, 404–407 (1990).
Sastry et al., *Proc. Natl. Acad. Sci. USA*, 86, 5728 (1989).
Schuster et al., *Biologie Prospective, C.R. Colloq. 8th*, 371–376 (1993).
Shirakawa et al., *Chest*, 95, 29–37 (1989).
Shirakawa et al., *Clin. Exp. Allergy*, 22, 213–218 (1992).
Shirakawa et al., *Clinical Allergy*, 18, 451–460 (1988).
Short et al., *Nucleic Acids Res.*, 16, 7583–7600 (1988).
Spitalny et al., *J. Exp. Med.*, 159, 1560–1565 (1984).
"Stability Constants of Metal Complexes A: Chelating Agents," at 404–405.
Stinson, *Chem. Eng. News*, 30–33 (Oct. 19, 1987).
Torchilin, et al., *Hybridoma*, 6, 229–240 (1987).
Tramontano et al., *Science*, 234, 1566–1569 (1986).
Treagan, *Biol. Trace Element Res.*, 1, 141–148 (1979).
Van Regenmorth, *T.I.B.S.*, 11, 36–39 (1986).
Van Vunakis, *Methods of Enzymology*, 70, 85–104 (1980).
Verhoeyan et al., *Science*, 239, 1534–1536 (1988).
Wade et al., *J. Am. Chem. Soc.*, 115, 4449–4456 (1993).
Waters et al., *DOE Methods for Evaluating Environmental and Waste Management Samples*, (1993).
Waters et al., *Govt. Reports Announcements & Index*, Issue 24 (1993).
Wide, et al., *BioChem. BioPhys. Acta.*, 130, 257–260 (1966).
Williams, *Nature*, 332, 393 (1988).
Wylie et al., *Anal. Biochem.*, 194, 381–387 (1991).
Wylie et al., *PNAS–USA*, 89, 4104–4108 (1992).
Wylie et al., *Proc. Natl. Acad. Sci.–USA*, 89, 4104–4108 (1992).
Yamamoto et al., *J. Immunol. Methods*, 22, 309=317 (1978).
Yanisch–Perron et al., *Gene*, 33, 103–119 (1985).
Yelton et al., *Hybridoma*, 5–11 (1981).

MERCURY-SPECIFIC ANTIBODY HEAVY CHAIN SEQUENCES

|  | | | | | | | | | 10 | | | | | | | | | | 20 | |
|---|---|---|---|---|---|---|---|---|---|---|---|---|---|---|---|---|---|---|---|---|
| 4A10 | Glu<br>GAG | Val<br>GTT | Gln<br>CAG | Leu<br>CTG | Gln<br>CAG | Gln<br>CAG | Ser<br>TCT | Gly<br>GGA | Pro<br>CCT | Glu<br>GAG | Leu<br>CTG | Val<br>GTG | Lys<br>AAG | Pro<br>CCT | Gly<br>GGG | Ala<br>GCT | Leu<br>TTA | Val<br>GTG | Lys<br>AAG | Ile<br>ATA |
| 1C11 | --- | --- | --- | --- | --- | --- | Ala<br>-G G-- | --- | --- | --- | -T --- | --- | --- | --- | --- | --- | Ser<br>-C- | --- | --- | Leu<br>--A C-G |
| 5G4 | --- | --- | --- | --- | --- | --- | Val<br>-T- | Ala<br>--G | Arg<br>-C- | Leu<br>-GN T-- | --- | --- | --- | --- | --- | --- | Ser<br>-C- | --- | Arg<br>-G- | --- |
| 23F8 | --- | --- | --- | --- | --- | --- | --- | --- | --- | --- | --A | --- | --- | Thr<br>A-- | --- | --- | Ser<br>-C- | --- | --- | --- |
| 2D5 | --- | --- | --- | --- | --- | --- | Gly Gly Ser<br>GGA -GC TCA | | | --- | --- | --- | --- | --- | --- | --A | Gly Ser Leu<br>-GG -CC C-- | | | --A C-C |
| 5B6 | --- | --- | --- | --- | --- | --- | Gly Gly Ser<br>GGA -GC TCA | | | --- | --- | --- | --- | --- | --- | --A | Gly Ser Leu<br>-GG -CC C-- | | | --- C-C |

FIG. 4A

```
                                         30                               CDR1              40
       Ser Cys Lys Ala Ser Gly Tyr Thr Phe Thr Ser Tyr Asp Ile Asn Trp Val Lys Gln Arg
       TCC TGC AAG GCT TCT GGT TAC ACC TTC ACA AGC TAC GAT ATA AAC TGG GTG AAG CAG AGG
4A10

Thr             Val                 Trp Met Gly
1C11   --- --- --- A-- --- --- --C --- G-- --- --C --- --- TGG --G GG- --- --- --- ---

Ala             Ser Gly             Phe Met                     Ser
5G4    --- --- --- --- --C --- --- --- T-A --T T-- G-- --- TT- --G --- --- --- --- --C

Ser Gly             Tyr Met His                 Ser
23F8   --- --- --- --- --- --- --- --- T-A --- --- T-- G-T T-C --G C-- --- --- --- --C

Ala         Phe     Ser         Cys Ala Met Ser             Arg Thr
2D5    --- --T GCA --C --- --- --A -T- --T --- -GT --- -GT -CC --G TCT --- --- --T CGC --CT

Ala         Phe     Ser         Arg Ala Met Ser             Arg Thr
5B6    --- --T GCA --C --- --- --A -T- --T --- -GT --- CGT -CC --G TCT --- --- --T CGC --CT
```

FIG. 4B

| | | | | | | | | | | 50 | | | 52A | | | | | | | CDR2 |
|---|---|---|---|---|---|---|---|---|---|---|---|---|---|---|---|---|---|---|---|---|
| 4A10 | Pro | Gly | Gln | Gly | Leu | Glu | Trp | Ile | Gly | Trp | Ile | Tyr | Pro | Gly | Asp | Gly | Ser | Thr | Lys | Tyr |
| | CCT | GGA | CAG | GGA | CTT | GAG | TGG | ATT | GGA | TGG | ATT | TAT | CCT | GGA | GAT | GGT | AGT | ACT | AAG | TAC |
| 1C11 | | | | | | | | | | | Asn | | | | Asp | Ser | Val | Thr | | Asn |
| | --- | --- | --A | --C | --- | --- | --- | --- | --- | --- | AAT | --- | --- | --- | -AT | AG- | --- | --C | --- | --C |
| 5G4 | His | Lys | Thr | | | | | | | | Arg | | | | Tyr | Asn | | Asp | | Phe |
| | -A- | A-- | ACC | --- | --- | --- | --- | --- | --- | --- | C-T | --- | --- | --- | TAC | A-- | --- | GA- | --- | TTC | --T |
| 23F8 | His | Lys | Ser | | | | | | | | Tyr | Ser | Cys | Tyr | Asn | | Ala | | | Ser |
| | -A- | A-- | A-C | --- | --- | --- | --- | --- | --- | --- | -AT | AG- | TG- | TAC | A-- | --- | GC- | --- | --- | -GC |
| 2D5 | Glu | Lys | Arg | | | | Val | Ala | Thr | | Ser | Ser | | Gly | Ser | Tyr | | | | Tyr |
| | --G | -AG | A-- | A-G | --- | --G | G-C | -C- | ACC | --- | AGC | AG- | --- | --T | -G- | A-- | TAC | --C | T-C | --T |
| 5B6 | Glu | Lys | Arg | | | | Val | Ala | Thr | | Ser | Ser | | Gly | Ser | Tyr | | | | Tyr |
| | --G | -AG | A-- | A-G | --- | --G | G-C | -C- | ACC | --- | AGC | AG- | --- | --T | -G- | A-- | TAC | --C | T-C | --T |

FIG. 4C

|        | 60                                          |           |           |           | 70                                          |           |           |           |           |
|--------|---------------------------------------------|-----------|-----------|-----------|---------------------------------------------|-----------|-----------|-----------|-----------|
| 4A10   | Asn Glu Lys Phe Lys Gly Lys Ala Thr Leu Thr Ala Asp Lys Ser Ser Ser Thr Ala Tyr<br>AAT GAG AAA TTC AAG GGC AAG GCC ACA CTG ACT GCA GAC AAA TCC TCC AGC ACA GCC TAC |
| 1C11   | --- --- --G --- --- --- --- --- --- --- --- -T- --- --- -T- --- --- --- -T- --- |
|        |                      Asn                    |           |           |           | Val                                         | Thr Phe   |           |           | Val       |
| 5G4    | --C C-- --G --- A-- --- --- --- --- --- --- -T- --- --- --- -T- --- --- --- C-- |
|        |                      Ser                    |           |           |           | Val                                         |           |           |           | His       |
| 23F8   | --C C-- --G --- --- --- --- --- --- T-- --- -T- --- --- -C- --- --- --- --- --- |
|        |                      Gln                    |           |           |           |                                             |           |           |           |           |
| 2D5    | Pro Asp Ser Val Arg Phe Ile Ser Arg His Asn Ala Glu Asn Leu<br>CCA --C -GT G-G --- --T CGA TT- --C A-C T-C AG- C-- --T G-- GAA -A- --C CTG |
|        |                      Phe Val Thr            |           |           |           |                                             |           |           |           |           |
| 5B6    | Pro Asp Ser Val Arg Phe Ile Ser Arg His Asn Ala Glu Asn Leu<br>CCA --C -GT G-G --- --T CGA TT- -CC A-C T-C AG- C-- --T G-- GAA -A- --C CTG |

| | 80 | | 82 | A | B | C | | | | | | | | | 90 | | | | | | | |
|---|---|---|---|---|---|---|---|---|---|---|---|---|---|---|---|---|---|---|---|---|---|---|
| 4A10 | Met<br>ATG | Gln<br>CAG | Leu<br>CTC | Ser<br>AGC | Ser<br>AGC | Leu<br>CTG | Thr<br>ACT | Ser<br>TCT | Glu<br>GAG | Asn<br>AAC | Ser<br>TCT | Ala<br>GCA | Val<br>GTC | Tyr<br>TAT | Phe<br>TTC | Cys<br>TGT | Ala<br>GCA | Arg<br>AGA | Cys<br>TGC | Gly<br>GGC | ---D---<br>Gly Val<br>GGG GTG | ---N--- |
| 1C11 | --- | --- | --- | --- | --- | --- | --A | --- | Asp<br>G-- | --- | --- | --- | --G | --- | Tyr<br>-AT | --- | --- | --- | ---<br>--- | ---<br>--- | ---<br>--- | ---N--- |
| 5G4 | --- | Glu<br>G-- | Leu<br>CTG | --- | --- | --- | --A | --- | Asp<br>G-- | --- | --- | --- | --- | --- | Tyr<br>-AT | --- | Gly<br>-G- | Thr<br>--C | Gln<br>CAG | Pro<br>CC- | --- | ---N--- |
| 23F8 | --- | Phe<br>T-- | Asn<br>-A- | --- | --- | --- | --A | --- | Asp<br>--A G-- | --- | --N | --- | --- | --- | Tyr<br>-A- | --- | --- | --- | Ser<br>TCC | Gly<br>G-G | --- | ---N--- |
| 2D5 | Leu<br>C-T | Met<br>--A A-G | --- | --- | --T | --- | Arg<br>-GG | --- | Asp<br>G-- | Thr<br>A-G | Ile<br>--C A-A | --- | --- | --- | Tyr<br>-AT | --- | Val<br>-TT | --- | Gln<br>CAG | Asp<br>GA- | --- | ---N--- |
| 5B6 | Phe<br>T-T | Met<br>--A A-G | --- | --- | --T | --- | Arg<br>-GG | --- | Asp<br>G-- | Thr<br>A-G | Ile<br>--- A-A | --- | --- | --- | Tyr<br>-AT | --- | Val<br>-TT | --- | Gln<br>CAG | Thr<br>ACG | --- | ---N--- |

|  | CDR3 | | | | | | | | | | | | |
|---|---|---|---|---|---|---|---|---|---|---|---|---|---|
|  | 100 | A | B | C | D | E | F | G | H | I | J | K | 101 |
| 4A10 | ... | ... | ... | ... | ... | ... | ... | ... | ... | Tyr Ala Met Asp Tyr Trp Gly Gln<br>TAT GCT ATG GAC TAC TGG GGT CAA | | | —J— |
| 1C11 | —N—\|———D———\|———N———\|<br>Tyr Ser Tyr Tyr Ser Tyr Asp Val<br>TAT AGT TAT TAC AGT TAC GAC GTC | | | | | | | | ... | Tyr Ala<br>TAT GCT ——— | | | —J— |
| 5G4 | Leu<br>CTT | ... | ... | ... | ... | ... | ... | ... | ... | \|——— | | | —J———C— |
| 23F8 | \|———————D———————\|<br>Ile Tyr Asp Gly Tyr Tyr<br>ATC TAT GAT GGT TAC TAC | | | | | | | ... | | Tyr Phe<br>TAC TTT ——— | | | —J———C— |
| 2D5 | \|————————D————————\|-N-\|<br>Gly Tyr Tyr Gly Asn Tyr Val<br>GGC TAC TAT GGC AAC TAC GTA | | | | | | | | ... | Trp Phe Ala<br>TGG TTT -CT | | | —J———C— |
| 5B6 | \|————————D————————\|-N-\|<br>Gly Tyr Tyr Gly Asn Tyr Glu<br>GGT TAC TAT GGC AAC TAC GAA | | | | | | | | ... | Trp Phe Ala<br>TGG TTT GCT | | | —J———C— |

FIG. 4F

```
          110
         Gly Thr Ser Val Thr Val Ser Ser
4A10     GGA ACC TCA GTC ACC GTC TCC TCA

1C11     --- --A --- --- --- --- --- ---

Thr Leu
5G4      --C --- A-T C-- --A --- --- ---

Thr Leu
23F8     --C --- A-T C-- --A --- --- ---

Leu                     Ala
2D5      --G --T CTG --- --T --- --T G--

Leu Leu                 Ala
5B6      --- CTT CTG --A --T --- --T G--
```

FIG. 4G

MERCURY-SPECIFIC ANTIBODY LIGHT CHAIN SEQUENCES

```
                                                    10
      Asp Ile Gln Met Thr Gln Ser Pro Ser Ser Leu Ser Ala Ser Leu Gly Glu Arg Val Thr
1F10  GAC ATC CAG ATG ACC CAG TCT CCA TCC TCC TTA TCT GCC TCT CTG GGA GAA AGA GTC ACT

Val Leu         Thr         Leu         Pro Val                 Asp Gln Ala Ser
4A10  --T G-T TT- --- --A A-- --- --- CT- --- C-G C-- -TC AG- --- --T CA- -C- T-C

Val Leu                 Ala             Ala Val                     Gln     Ser
1C11  --- T-A GT- C-T --A --- --- C-T --- --T --- G-- -TA --- --- --G C-G --G TC- ---C

5G4   --- --- --- --- --- --- --- --- --- --- --- --- --- --- --- --- --- --- --- ---

--A C-G     --A                     Gly Lys
23F8  --- --- --- --- --- --- --- --- --- --- --- --- --- --- --- --- --- -GC --A --C

Glu Leu Val             Ala             C--     --A             Val         Thr
2D5   --G C-- GT- --- --- --- G-- --- --- --- --- --- --- --- --- G-- --- --- -CT ---C

|  |  |  |  |  |  |  |  | CDR1 |  |  |  |  |  |  |
|---|---|---|---|---|---|---|---|---|---|---|---|---|---|---|---|
|  | 24 | 25 | 26 | 27 | A | B | C | D | E | 28 |  |  | 30 |  |  |
| 1F10 | Leu | Thr | Cys | Arg | Ala | Ser | Gln | ... | ... | Asp | Ile | Gly | Ser | Ser | Leu | Asn | Trp |
|  | CTC | ACT | TGT | CGG | GCC | AGT | CAG | ... | ... | GAC | ATT | GGT | AGT | AGT | TTA | AAC | TGG |
| 4A10 | Ile | Ser |  |  | Ser | Ile | Val | His | Ser | Asn | Gly | Asn | Thr | Tyr |  | Glu |  |
|  | A-- | T-- | --C | A-A | T-T | --- | --- | AGC | ATT | GTA | CAT | AGT | A-T | GGA | AAC | --CC | TA- | --- | G-A | --- |
| 1C11 | Ile | Ser |  |  |  | Ser | Val | Asn | Thr | Ser | Ser | Tyr |  | Cys |  | His |  |
|  | A-- | --- | --C | A-- | --- | --C | --A | AGT | GTC | AAT | ACA | ... | A | AGT | TCT | -GC | TA- | --- | T-- | --G | C-- | --- |
| 5G4 |  |  |  |  |  |  |  | ... | ... |  |  |  |  |  |  |  |  |
| 23F8 | Ile |  |  | Lys |  |  |  |  |  |  | Asn | Lys | Tyr | Ile | Ala |  |
|  | A-- | --- | --C | AA- | --A | --C | --A | ... | ... |  | --- | AAC | -AG | TA- | A-- | --- | GCT | --- |
| 2D5 | Ile |  |  | Glu |  |  |  |  |  | Asn |  | Tyr | Gly | Tyr |  | Ala |  |
|  | A-- | --A | --- | G-- | --A | --- | --A | ... | ... | A-T | --- | TAC | G-- | TA- | --- | GCA | --- |
| 5B6 |  |  |  |  |  |  |  |  |  |  |  |  |  |  |  |  |

|  |  | 40 |  |  |  |  |  |  |  |  |  | 50 |  |  | CDR2 |  |  |
|---|---|---|---|---|---|---|---|---|---|---|---|---|---|---|---|---|---|
|  | Leu | Gln | Leu | Lys | Pro | Asp | Gly | Thr | Ile | Lys | Arg | Leu | Ile | Tyr | Ala | Thr | Ser | Gly | Leu | Asp |
| 1F10 | CTT | CAG | CTG | AAA | CCA | GAT | GGA | ACT | ATT | AAA | CGC | CTG | ATC | TAC | GCC | ACA | TCC | GGT | TTA | GAT |
|  |  | Tyr | Leu | Gln |  |  | Gly | Gln | Ser | Pro |  | Leu |  |  | Lys | Val |  | Asn | Arg | Phe |
| 4A10 | TAC | -T- | -A- | --- | --- | -GC | CAG | T-- | CCA | --G | -T- | --- | --- | AAA | GTT | --- | AAC | CG- | TT- |
|  |  | Tyr | Gln | Asn |  |  | Gly | Gln | Pro | Pro |  | Leu |  |  | Lys | Tyr | Ala |  | Asn | Glu |
| 1C11 | TAC | --A | -A- | --T | --- | -GG | CAG | C-A | CCG | --- | -T- | --- | --C | A-G | TAT | G-- | --- | AAC | C-- | --A |
| 5G4 | --- | --- | --- | --- | --- | --- | --- | --- | --- | --- | --- | --- | --- | --- | --- | --- | --- | --- | --- | --- |
|  |  | Tyr | His |  |  | Gly | Lys | Gly | Pro | Arg | Leu |  |  | His | Tyr |  |  | Thr | Gln |
| 23F8 | TAC | --A | -AC | --G | --T | -GA | AA- | GG- | CC- | -GG | -TG | --C | --A | C-T | TA- | --- | --T | ACA | --- | C-G |
|  |  | Tyr | Gln |  |  | Gln | Gly | Lys | Ser | Pro | Leu | Pro | Arg | Val |  | Asn | Ala | Lys | Thr | Ala |
| 2D5 | TA- | --- | -A- | --- | --- | -AG | -GA | AA- | T-- | CC- | CTG | -C- | -G- | G-- | --T | AAT | G-- | --T | AAA | ACC | --CA |
| 5B6 | --- | --- | --- | --- | --- | --- | --- | --- | --- | --- | --- | --- | --- | --- | --- | --- | --- | --- | --- | --- |

|  |  |  |  |  |  |  |  |  | 60 |  |  |  |  |  |  |  |  |  | 70 |  |  |  |  |  |  |
|---|---|---|---|---|---|---|---|---|---|---|---|---|---|---|---|---|---|---|---|---|---|---|---|---|---|---|
| 1F10 | — | Ser<br>TCT | Gly<br>GGT | Val<br>GTC | Pro<br>CCC | Lys<br>AAA | Arg<br>AGG | Phe<br>TTC | Ser<br>AGT | Gly<br>GGC | Ser<br>AGT | Arg<br>AGG | Ser<br>TCT | Gly<br>GGG | Ser<br>TCA | Asp<br>GAT | Tyr<br>TAT | Ser<br>TCT | Leu<br>CTC | Thr<br>ACC | Ile<br>ATC |
| 4A10 | | --- | --G | --- | Asp<br>--A G-C | --- | --- | --- | --- | --- | --- | Gly<br>G-A | --- | --A | Thr<br>A-- | --- | Phe<br>-TC | Thr<br>A-A | --- | Lys<br>-AG | --- |
| 1C11 | | --- | --G | --- | Ala<br>--T GCC | --- | --- | --- | --- | --- | --- | Gly<br>G-- | --- | --- | Thr<br>A-- | --C | Phe<br>-TC | Thr<br>A-C | --- | -A- | --- |
| 5G4 | | --- | --- | --- | --- | --- | --- | --- | --- | --- | --A | --- | --- | --- | --- | --- | --- | --- | --- | --- | --- |
| 23F8 | | Pro<br>C-A | Ile<br>A-- | Ser<br>--A TC- | --- | --- | --- | --- | --- | --- | --- | Gly<br>G-- | --- | --- | Arg<br>AG- | --- | --- | --C | Phe<br>T-- | Ser<br>-G- | --- |
| 2D5 | | Glu Asp<br>GAG -A- | Ser Ser<br>--G T-A TC- | Val<br>G-- | --- | --- | --- | --- | --- | --- | --- | Gly<br>G-A--CA | --C | Thr Gln Phe<br>A-A C-G -T- | --- | --G | -AG | --- |
| 5B6 | | --- | --- | --- | --- | --- | --- | --- | --- | --- | --- | --- | --- | --- | --- | --- | --- | --- | --- | --- | --- |

FIG. 5D

|      |     |     |     |     |     |     |     |     |     | 80  |     |     |     |     |     |     |     |     |     |     |     |     |     |     | 90  |     | CDR3 |     |     |     |
|------|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|
| 1F10 | Asn | Ser | Leu | Glu | Ser | Glu | Asp | Phe | Val | Asp | Tyr | Tyr | Cys | Leu | Gln | Cys | Ser | Asn | Ser | Pro |
|      | AAC | AGC | CTT | GAG | TCT | GAA | GAT | TTT | GTA | GAC | TAT | TAC | TGT | CTA | CAA | TGT | TCT | AAT | TCT | CCG |
| 4A10 |     | Ser | Arg | Val |     | Ala |     |     | Leu | Gly | Val |     |     |     | Phe |     | Gly |     | His | Val | Arg |
|      | -G- | --A | G-G | --- | --- | -AG | --- | --- | C-G | -G- | -TT | --- | --- | --C | T-T | -A- | G-- | --A | C-- | GT- | -G- |
| 1C11 |     | His | Pro | Val |     | Val |     |     | Ser | Ala | Thr |     | Phe |     | Gln | His | Ser | Trp | Glu | Ile |
|      | C-T | CCT | G-G | -A- | GTG | --- | --- | --- | AG- | -C- | ACA | --- | -T- | --- | -A- | --C | A-- | -GG | G-G | AT- | --T |
| 5G4  | --- | --- | --- | --- | --- | --- | --- | --- | --- | --- | --- | --- | --- | --- | --- | --- | --- | --- | --- | --- | --- |
| 23F8 |     | Ser | Asn |     |     | Pro |     |     | Ile | Ala | Thr |     |     |     |     |     | Tyr | Asp |     |     | Leu |
|      | -G- | --A | --G | --- | --- | -C- | --- | --- | A-- | -C- | ACT | --- | --T | --- | --G | --A | -GA | --- | --- | ... | CTG |
| 2D5  |     | Arg | Thr | Gln | Pro |     |     |     | Gly | Thr |     |     |     |     | Gln | His | His | Tyr | Gly | Thr |
|      | -GG | -CA | T-G | C-- | C-- | --- | --- | --- | --- | -GG | ACT | --- | --- | --- | -A- | --T | CA- | -A- | GG- | A-- | --- |
| 5B6  | --- | --- | --- | --- | --- | --- | --- | --- | --- | --- | --- | --- | --- | --- | --- | --- | --- | --- | --- | --- | --- |

FIG. 5E

|  | | | | | | 100 | | | | J | | | |
|---|---|---|---|---|---|---|---|---|---|---|---|---|---|
|  | Tyr | Thr | Phe | Gly | Gly | Gly | Gly | Thr | Lys | Leu | Glu | Ile | Lys |
| 1F10 | TAC | ACG | TTC | GGA | GGG | GGG | ACC | AAG | CTG | GAA | ATA | AAA |
| 4A10 | ... | --- | --- | --- | --T | --A | --C | --- | --- | --- | --C | --- |
| 1C11 | Pro<br>CCG | --- | --- | --- | --T | --A | --C | --- | T-- | --- | --C | --- |
| 5G4 | --- | --- | --- | --- | --- | --- | --- | --- | --- | --- | --- | --- |
| 23F8 | Phe<br>-T- | --- | --- | Ser<br>-C TC- | --- | --A | --- | T-- | --- | --- | --- |
| 2D5 | --- | --- | --- | --- | --- | --- | --- | --- | --- | --- | --- | --- |
| 5B6 | --- | --- | --- | --- | --- | --- | --- | --- | --- | --- | Asn<br>--C |

FIG. 5F ured by contaminants. The sensi-
MERCURY BINDING POLYPEPTIDES AND NUCLEOTIDES CODING THEREFORE

CROSS REFERENCE TO RELATED APPLICATIONS

This application is a continuation of Ser. No. 08/187,407, filed Jan. 27, 1994, now abandoned, which is a continuation-in-part of Ser. No. 07/990,542, filed Dec. 14, 1992, U.S. Pat. No. 5,503,987, which is a continuation of Ser. No. 07/493,299, filed Mar. 14, 1990, now abandoned, which is a continuation-in-part of Ser. No. 07/324,392, filed Mar. 14, 1989, now abandoned, all of which files are herein incorporated by reference.

BACKGROUND OF THE INVENTION

Small chemical moieties, such as heavy metal ions, can and often do affect the environment and biological systems. These effects become astounding when it is realized that minute quantities of these small moieties are involved. Moreover, the presence or absence of low concentrations of small moieties in the environment can have long term consequences. Minute quantities of metallic cations, such as mercury cations, can regulate, influence, change or toxify the environment or biological systems.

The detection, removal, addition or neutralization of such minute quantities constitutes a focal point for continued research in many fields. For example, many efforts have been made to detect and remove minute, toxic amounts of heavy metal ions such as cadmium or mercury from the environment. The efforts often have not been successful or economical for widespread application. On the other hand, minute concentrations of other heavy metals are important for the proper function of biological organisms. Zinc, for example, plays a major role in wound healing. The function of magnesium in plant photosynthesis is another.

Heavy metal can exhibit dual roles. Mercury is used in diuretics, topical anti-bacterial agents, skin antiseptics, ointments, and in chemical manufacturing operations. Yet when ingested by mammals, such as from drinking water, it is highly toxic in very small amounts. Hence, detection and quantification of minute concentrations of heavy metals in drinking water and other media would serve exploratory, safety and regulatory goals.

It would, therefore, be highly desirable to identify and control minute quantities of heavy metals, e.g., mercury cations, in aqueous biological or inanimate systems. In most contexts, however, the detection, removal, addition or neutralization of heavy metals, is a difficult and expensive and often unfeasible if not impossible task. Other metallic contaminants often mimic the heavy metal of interest. Measurement interference will result. Moreover, the detection methods employed today are usually not sufficiently sensitive at the minute quantities under consideration. Consequently, it is desirable to develop reliable and economic methods for accurately identifying and controlling minute quantities of heavy metals in aqueous systems.

Antibodies would seem to be uniquely suited for this task. Their high degree of specificity for a known antigen would avoid the interference caused by contaminants. The sensitivity of antibodies in the picomolar or lower range would permit accurate and efficient targeting and detection of such minute levels.

Monoclonal antibodies, of course, come to mind as especially suited agents for practice of this technique. Since Kohler and Milstein published their article on the use of somatic cell hybridization to produce monoclonal antibodies (*Nature* 256:495 (1974)), immunologists have developed many monoclonal antibodies which strongly and specifically immunoreact with antigens.

Notwithstanding this suggestion, the conventional understanding about immunology teaches that antibodies against small moieties, such as heavy metals, cannot be developed. The mammal immunization step, which is key for the production of monoclonal antibodies, typically requires a molecule that is large enough to cause antigenic reaction. Medium sized molecules (haptens), which are not of themselves immunogenic, can induce immune reaction by binding to an immunogenic carrier. Nevertheless, immunologists view small moieties such as metallic cations, as not large or structurally complex enough to elicit an antibody response. One theory appears to hold that electron rich rings such as those associated with benzene and carbohydrates are needed at a minimum to cause immunogenicity. V. Butler, S. Beiser, *Adv. Immunol.*, 17, 255 (1973). The molecular size and lack of complexity of an inorganic moiety is thought to render it insufficient for eliciting an antibody response. To date, therefore, no monoclonal antibodies which immunoreact with mercury cations per se have been reported in the literature.

Several immunologists have reported production of monoclonal antibodies to metallic ion chelates. For example, in U.S. Pat. No. 4,722,892, monoclonal antibodies are disclosed which immunoreact with a complex of a chelating agent, such as ethylene diamine tetracetate (EDTA), and a heavy metal such as indium. In EPO Patent Application 0235457, monoclonal antibodies that immunoreact with a chelate of gold cyanate and carbonate coating are disclosed. In these instances, however, the monoclonal antibodies bind with the metal chelate complex rather than the bare metallic ion itself. Disadvantages of these methods include: the complicated reagents involved in detection, lack of simple tests that discriminate among antigens, cross-reactivity with chelates of other antigens and cross-reactivity with the chelate itself.

Other instances of monoclonal antibody combinations with metals involve metal tags. The metal chelates are bound to the antibody at a site remote from the antigen binding site or sites. The metal or metal chelate is not the antigen. Instead, it is a tag to indicate the presence of the monoclonal antibody when it reacts with its specific antigen. See for example, V. P. Torchilian et al., *Hybridoma*, 6, 229 (1987); and C. F. Meares, *Nuclear Medical Biology*, 13, 311–318 (1986).

It is therefore, an object of the invention to develop polypeptides that immunoreact with heavy metals per se and with mercury ions in particular. It is another object of the invention to develop methods for detecting or neutralizing heavy metals within, adding heavy metals to, or removing heavy metals from biological or inanimate systems through the use of the monoclonal antibodies. Further objects include the development of nucleic acid sequences coding for polypeptides which immunoreact with mercury cations and the development of methods of expressing these nucleic acid sequences to produce metal binding polypeptides.

SUMMARY OF THE INVENTION

These and other objects are achieved by the present invention which is directed to a metal binding polypeptide which immunoreacts with a heavy metal, such as a mercury cation. The metal binding polypeptide includes an amino acid sequence for a variable region from a monoclonal antibody, wherein the monoclonal antibody immunoreacts with a mercury cation. For example, the metal binding polypeptide may include an amino acid sequence for a heavy chain Fd fragment (consisting of the heavy-chain variable region and heavy-chain constant region 1 domains) from the monoclonal antibody. The metal binding polypeptide may further include a heavy chain Fc fragment fused to the heavy chain Fd fragment or a phage coat protein or portion thereof fused to the heavy chain Fd fragment. Alternatively, the metal binding polypeptide may include an amino acid sequence for a light chain from the monoclonal antibody.

In another embodiment, the present invention provides a fusion protein which includes a phage coat protein or portion thereof fused to an amino acid sequence for a heavy chain variable region from the monoclonal antibody. The fusion protein preferably includes the heavy chain Fd fragment of the monoclonal antibody. The fusion protein may be present as part of the coat of a phage and, preferably, the coat of a filamentous phage.

The invention is also directed to a heavy chain of the monoclonal antibody. The heavy chain preferably includes a sequence selected from a group of the sequences for the heavy chain variable region of certain specified monoclonal antibodies. The invention is also directed to a light chain of the monoclonal antibody. As with the heavy chain, the light chain preferably includes a sequence selected from a group of the sequences for the light chain variable region of certain specified monoclonal antibodies.

Another embodiment of the invention provides a recombinantly produced Fab fragment that immunoreacts with a mercury cation. The recombinantly produced Fab fragment includes an amino acid sequence for a variable region from the monoclonal antibody which immunoreacts with the mercury cation. Preferably, the Fab fragment includes a heavy chain Fd fragment or a light chain from the monoclonal antibody.

The present invention also provides a monoclonal antibody which includes a Fab fragment. The Fab fragment immunoreacts with a mercury cation and includes an amino acid sequence selected from a group of sequences for the variable regions of certain specified monoclonal antibodies. The Fab fragment heavy chain preferably includes an amino acid sequence selected from a group of the sequences for the heavy chain variable region of the specified monoclonal antibodies. In another preferred embodiment, the Fab fragment light chain includes an amino acid sequence selected from a group of the sequences for the light chain variable region of the specified monoclonal antibodies. The monoclonal antibody may be a recombinantly produced monoclonal antibody.

Yet another embodiment of the invention is directed to an isolated nucleic acid sequence coding for a variable region of a monoclonal antibody, e.g., the heavy chain variable region or the light chain variable region of the monoclonal antibody. The monoclonal antibody immunoreacts with a mercury cation. Alternatively, the isolated nucleic acid sequence may code for the heavy chain Fd fragment, the entire heavy chain or the entire light chain of the monoclonal antibody.

The present invention is also directed to an expression cassette. The expression cassette includes a nucleic acid sequence coding for a variable region of the monoclonal antibody which immunoreacts with a mercury cation. The nucleic acid sequence coding for the variable region is operably linked to a promoter functional in a vector. The expression cassette may include the promoter operably linked to a nucleic acid sequence coding for a heavy chain Fd fragment of the monoclonal antibody. Alternatively, the expression cassette may include the promoter operably linked to a nucleic acid sequence coding for a light chain of the monoclonal antibody. The expression cassette may also include a leader sequence located between the promoter and the nucleic acid sequence coding for the monoclonal antibody chain. The leader sequence functions to direct the heavy or light chain to a membrane in a host cell.

Another embodiment of the present invention is directed to an expression cassette coding for a fusion protein. This expression cassette includes a first nucleic acid sequence coding for a heavy chain Fd fragment of a monoclonal antibody. The monoclonal antibody reacts with a mercury cation. The first nucleic acid sequence is linked for co-expression to a second nucleic acid sequence coding for a phage coat protein or a portion thereof to form a nucleic acid sequence encoding the fusion protein. The fusion protein includes the heavy chain Fd fragment fused to the phage coat protein or portion thereof. The expression cassette coding for the fusion protein also includes a promoter that is functional in a vector. The promoter is operably linked to the first and second DNA sequences and provides for expression of the fusion protein. The expression cassette may also include a leader sequence which directs expression of the fusion protein to a membrane of a host cell. The leader sequence is located between the promoter and the nucleic acid sequence coding for the fusion protein. In addition, the expression cassette may include a third nucleic acid sequence coding for a peptide linker. The third nucleic acid sequence is typically located between the first and second nucleic acid sequences. The expression cassette may optionally include a fourth nucleic acid sequence coding for a light chain of a monoclonal antibody. Preferably, the light chain is a light chain of a monoclonal antibody that immunoreacts with a mercury cation.

The present invention also is directed to a phagemid vector which includes one of the expression cassettes described above.

The invention is further directed to methods for detecting, removing, adding, or neutralizing the heavy metals in biological, and inanimate systems through the use of the metal binding polypeptides, heavy and light chains, fusion proteins, recombinantly produced Fab fragments and monoclonal antibodies described above.

The advantages of the invention include among others: the lack of complication by additional reagents, a high discrimination against similar antigenic materials, lack of cross-reactivity with similar antigenic materials, and lack of cross-reactivity with test reagents.

The metal binding polypeptide of the invention immunoreacts with a heavy metal per se, and preferably with a mercury cation per se. The state of the heavy metal during this immunoreaction is one of non-coordination with any other substance; in other words, it is bare or exposed. Preferably, the metal binding polypeptide exhibits a substantially high degree of specific immunoreactivity toward the heavy metal. Also preferably, the metal binding polypeptide includes a portion of a recombinantly produced Fab fragment (e.g., the light chain or the heavy chain Fd fragment of the Fab fragment) and has an association constant for a heavy metal such as a mercury cation that is about 10,000 fold greater than the association constant for the immunogen compound without the heavy metal. Also preferably, the metal binding polypeptide is immunospecific for a particular member of a group of very similar heavy metals. The monoclonal antibody will exhibit a relative association constant for such a particular heavy metal that is about 10,000 fold greater than that for the other heavy metals of such a group.

The hybridoma of the invention, which produces the monoclonal antibody, is formed from immune cells that are specific for the heavy metal. The formation is accomplished by fusion of an immortal mammal cell line and mammal immune cells from a second mammal previously immunized with an immunogen compound which contains the heavy metal. Selection of the appropriate hybridoma is determined by cross-screening the secreted monoclonal antibody against the heavy metal and against controls which incorporate the heavy metal or very similar congeners.

The immunogen compound of the invention is composed of a biopolymer carrier, a spacer arm covalently bonded to the carrier and the heavy metal coordinated to the spacer arm. The spacer arm is semi-rigid and has at least one heavy metal coordination site. This arrangement maintains the heavy metal in at least a partially exposed state and prevents substantially complete inclusion or chelation of the heavy metal by spacer arm and/or carrier.

The biopolymer carrier may be a polysaccharide, a synthetic polyamide or preferably a protein. Preferred classes include blood or tissue sera proteins.

The spacer arm is no more than about 25 atoms in length. It is composed of one of three classes: an oligopeptide, an aliphatic compound or an aliphatic fragment and, preferably, is an oligopeptide. The first two classes are each substituted with no more than about 2 pendent Lewis acid or base groups, and a coupling group for forming a covalent bond with the protein carrier. The aliphatic fragment is substituted by a coupling group for forming a covalent bond with the protein carrier, and a carboxylic acid, hydroxyl, mercapto, amine or other group adapted for interacting with the heavy metal. For each class of spacer arm, the coupling group is an amine, carboxylic acid, aldehyde, hydroxyl or mercapto group.

A preferred spacer arm for metallic cations is an oligopeptide or aliphatic compound having no more than about 2 pendent Lewis base groups wherein the deformation of the electron shell of the Lewis base group is approximately of the same character as the deformation of the electron shell of the metallic cation. Especially preferred Lewis base groups for transition elements and the heavy metals are those containing sulfur. Especially preferred are oligopeptides such as glutathione and cysteine, mercapto ethanol amine, dithiothreitol, amines and peptides containing sulfur, and the like.

The metallic cations are derived from metals such as period four transition metals, and period five, six and seven metals, transition elements and inner transition elements. The metallic cations of special mention as the heavy metal include those derived from zinc, lead, cadmium, bismuth, cobalt, arsenic, chromium, copper, nickel, strontium and mercury. Preferably, the metallic cations are mercury cations, e.g. mercuric cations.

The methods according to the invention utilize the metal binding polypeptide for detection, removal, neutralization or addition of the heavy metal respectively in, from, within or to a liquid or gaseous medium. These methods utilize features such as metal binding polypeptide immobilization, heavy metal immobilization, competitive binding, and means employing an oscillating probe, a micromagnetic probe and other physiochemical methods typically used to monitor antigen-antibody interactions.

Methods for detection that are based upon heavy metal immobilization may indicate the presence of the heavy metal-metal binding polypeptide conjugate (e.g., a mercuric cation-Fab fragment conjugate) by known immunologic assay techniques. In a first step, the heavy metal is coordinated with an immobilized spacer arm for the heavy metal. The spacer arm can be any of the foregoing that will hold the heavy metal in at least a partially exposed state. It need not be the same spacer arm of the immunogen compound used to develop the metal binding polypeptide. Non-immobilized materials are then removed from the mixture holding the immobilized spacer arm-heavy metal. Addition of the metal binding polypeptide (e.g., Fab fragment), removal of uncomplexed metal binding polypeptide and immunoassay complete the steps for this detection method.

Methods for detection that are based upon an immobilized metal binding polypeptide may utilize a radioactive version of the heavy metal or a similar tagged form thereof. Such tags include fluorescent, calorimetric and other spectrally active groups that can be coordinated or bonded to the heavy metal like the spacer arm. A preferred tag is a spacer arm containing a spectrally active group. First, the immobilized monoclonal antibody is saturated with the tagged heavy metal. After removal of the non-immobilized components, an aliquot of the unknown heavy metal is added. It displaces a portion of the bound, tagged heavy metal and measurement of that amount displaced will determine the concentration of unknown metal.

Methods for detection that are based upon an oscillating probe utilize either an immobilized spacer arm for the heavy metal or preferably immobilized metal binding polypeptide. This method measures the change in frequency of an oscillating surface as a function of the change in weight of that surface due to the binding of the non-immobilized heavy metal or metal binding polypeptide. In the preferred method the metal binding polypeptides are immobilized on the surface of a high frequency oscillating probe. The probe is placed into a medium containing an unknown quantity of heavy metal. Binding of the heavy metal to the immobilized metal binding polypeptide will change the oscillation frequency of the probe. Hence, the degree of change will indicate the level of heavy metal present.

When the heavy metal is present as a metal cation in an aqueous medium, an especially preferred method for detection utilizes an oligopeptide having reactive sulfhydryl group(s) capable of coordinating with the metal cation. The oligopeptide and the metal binding polypeptide specific for the metal cation unknown are added to the aqueous medium. The medium then is assayed for the presence of metal binding polypeptide cation conjugate. The interaction of the metal binding polypeptide with the metal cation is independent of the order of addition of the reactants and is independent of the identity of the oligopeptide.

In an especially preferred version of this method, a fixed support is utilized. Here, either the oligopeptide or the metal binding polypeptide is immobilized on the fixed support. The method is then conducted as related above.

The invention, in addition, contemplates methods for heavy metal removal from, heavy metal neutralization within or heavy metal addition to biological or inanimate systems. For all methods, an effective amount of the metal binding polypeptide is combined in some fashion with at least part of the system. Pursuant to the removal method, metal binding polypeptide-heavy metal conjugate is removed by separation means such as immunoprecipitation, immobilization, chromatography, filtration and the like. Pursuant to the neutralization method, the metal binding polypeptide-heavy metal conjugate remains in the system until it is removed by non-specific means. Pursuant to the addition method, the metal binding polypeptide-heavy metal conjugate also remains in the system and the heavy metal is actively incorporated or otherwise used therein.

When the system participating in the foregoing methods is biological, the metal binding polypeptide may be combined with a pharmaceutically acceptable carrier. Preferably, the metal binding polypeptide will not of itself cause an undesirable immune response of the biological system. The biological systems contemplated according to the invention include unicellular organisms, multicellular simple organisms, cellular component systems, tissue cultures, plants and animals, including mammals.

The present invention also contemplates methods for removing heavy metallic cations or radioactive compounds from human fluids such as blood, serum or lymph by utilization of immobilized monoclonal antibodies. An extracorporeal shunt placed in the patient permits removal of the body fluid and its reintroduction. Passing the body fluid extracorporeally through a bed of immobilized metal binding polypeptide accomplishes the desired removal.

When a method for adding a metal binding polypeptide-heavy metal conjugate to a biological or inanimate system is contemplated, the metal binding polypeptide will preferably be bifunctional. The second binding site of the metal binding polypeptide will be reactive with a selected component of the system. That component may be a complex organic molecule, living cells, selected tissue of a tissue culture or a selected tissue of an animal. In this method, the heavy metal will exert a desirable action upon the component of the biological or inanimate system targeted.

The present invention also contemplates a kit for assaying the presence and quantity of heavy metal in a biological or inanimate system. The kit includes aliquots of metal binding polypeptides in the appropriate buffer, as well as a fixed support for absorption of the heavy metal, washing solutions, reagents such as enzyme substrates, and metal binding polypeptide specific antisera conjugated to a detectable substrate.

BRIEF DESCRIPTION OF THE DRAWINGS

FIG. 4A depicts the nucleotide and deduced amino acid sequences for amino acids 1 through 59 of the heavy chain variable regions of monoclonal antibodies which immunoreact with a mercury cation. The gaps from positions 1 to 6 in all the antibodies except mAb 4A10 correspond to the primers used for PCR amplification. Since these sequences in the antibodies are not known with certainty, they were omitted from the Figure. The cysteine residues thought to be important for mercury binding are shown encircled. The numbering scheme is according to Kabat et al., Sequences of Proteins of Immunological Interest, vol. II. 5th edition, U.S. Department of Health and Human Services (1991). Dashes indicate sequence identity with the 4A10 sequence; periods indicate gaps compared to 4A10.

FIG. 4B depicts the nucleotide and deduced amino acid sequences for amino acids 60 through 105 of the heavy chain variable regions of the monoclonal antibodies of FIG. 4A. The cysteine residues thought to be important for mercury binding are shown encircled. Dashes indicate sequence identity with the 4A10 sequence; periods indicate gaps compared to 4A10.

FIG. 4C depicts the nucleotide and deduced amino acid sequences for amino acids 106 through 113 of the heavy chain variable regions of the monoclonal antibodies of FIGS. 4A and 4B. The cysteine residues thought to be important for mercury binding are shown encircled. Dashes indicate sequence identity with the 4A10 sequence; periods indicate gaps compared to 4A10.

FIG. 5A depicts the nucleotide and deduced amino acid sequences for amino acids 1 through 55 of light chain variable regions of monoclonal antibodies which immunoreact with a mercury cation. The cysteine residues thought to be important for mercury binding are shown encircled. The numbering scheme is according to Kabat et al. Dashes indicate sequence identity with the 1F10 sequence; periods indicate gaps compared to 1F10.

FIG. 5B depicts the nucleotide and deduced amino acid sequences for amino acids 56 through 107 of light chain variable regions of the monoclonal antibodies of FIG. 5A. The cysteine residues thought to be important for mercury binding are shown encircled. Dashes indicate sequence identity with the 1F10 sequence; periods indicate gaps compared to 1F10.

DETAILED DESCRIPTION OF THE INVENTION

Figure 1:
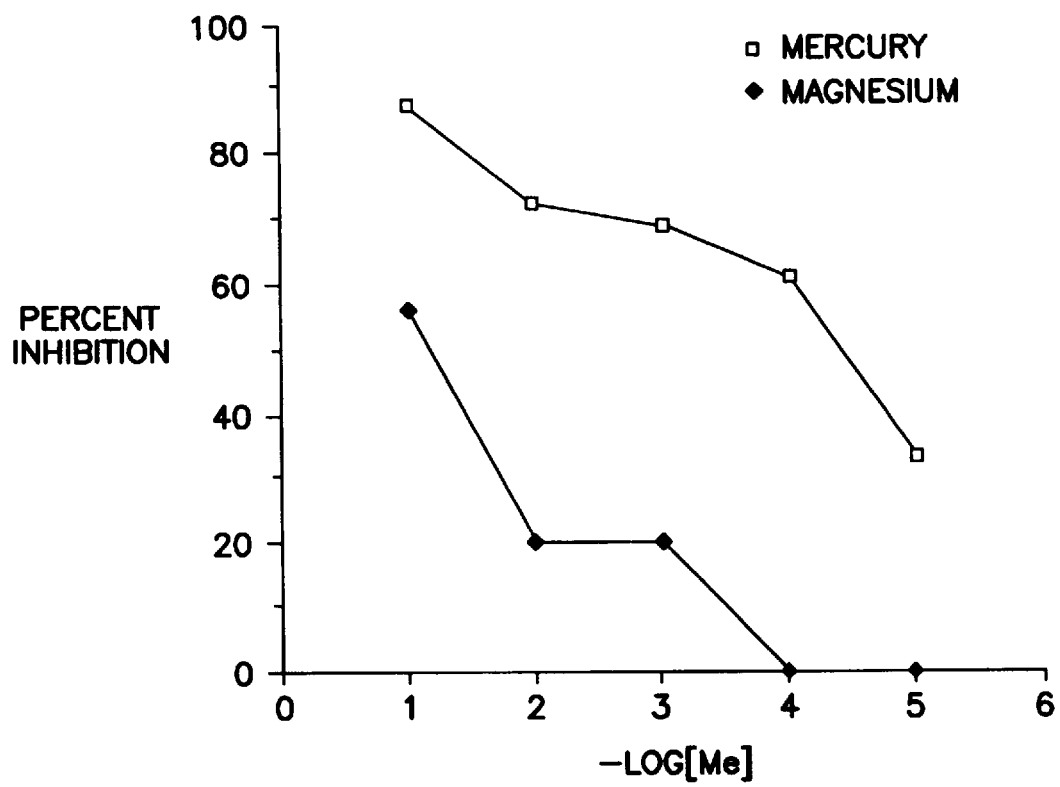
FIG. 1 shows a graph of the results of an immunosorbent assay. The results depict the competitive binding of mercuric ion and magnesium ion for a monoclonal antibody to mercury.

Metal binding polypeptides of the present invention are key to the development of methods for detecting, adding, neutralizing or removing minute quantities of heavy metals. Until the present invention, it was not possible to produce metal binding polypeptides which immunoreact with exposed heavy metal cations per se. The novel techniques for incorporating heavy metals into immunogen compounds and for administering these immunogen compounds to immune cell hosts allow production of the desired, immunospecific monoclonal antibodies according to the invention. These methods are believed to constitute an advancement in the understanding of immunology.

Although not intended as a limitation of the invention, it is now believed that mammalian immunogenic reactivity can be elicited by heavy metals. While they are smaller than the commonly recognized epitopal size of approximately 20–25 angstroms, the heavy metals nevertheless can epitopally bind.

Notwithstanding these beliefs, the invention contemplates metal binding polypeptides which immunoreact with a heavy metal, e.g. monoclonal antibodies to heavy metals. The hybridomas for the monoclonal antibodies and the immunogen compounds for carrying the heavy metals and inducing immunogenicity are also included. The metal binding polypeptides may include a monoclonal antibody, a recombinantly produced Fab fragment or a fusion protein. The fusion protein includes the heavy chain variable region, of a monoclonal antibody, wherein the monoclonal antibody immunoreacts with a heavy metal such as a mercury cation.

The invention also provides methods for the detection, addition, neutralization or removal of heavy metals using the metal binding polypeptides.

Monoclonal Antibodies

The monoclonal antibodies of the invention are mammalian immunoglobulin proteins which have strong affinity constants for a specific heavy metal. Preferably, they are from the IgG, IgA, IgM and IgE classes of immunoproteins. They are characterized by selective immunoreactivity with a particular heavy metal and a substantially lower immunoreactivity with other similarly structured heavy metals. Preferably, the monoclonal antibodies have an association constant for the selected heavy metal that is at least about 10,000 fold greater than the association constant for the similarly structured heavy metal. With respect to heavy metal cations, the especially preferred IgG class of monoclonal antibodies of the present invention exhibit discriminatory dissociation constants of about $10^{-6}$ to about $10^{-12}$. One example is a monoclonal antibody of the IgA class which is produced by hybridoma 1F10, and has a dissociation constant for mercury cation of less than about $10^{-9}$ but does not bind cadmium, copper, zinc, lead, nickel and cobalt cations to any appreciable extent. Another example is a monoclonal antibody of the IgG class which is produced by hybridoma 5H1, and has a dissociation constant for lead cation of less than about $10^{-9}$ but does not bind cadmium, copper, zinc, mercury, nickel and cobalt cations to any appreciable extent.

Immunogen Compounds

The immunogen compounds for generation of the specific immunogenicity of the monoclonal antibodies are based upon the hapten-carrier concept. The present invention, however, broadens this concept so that the hapten is coordinated at the end of a spacer arm covalently bonded to the carrier. The spacer arm is adapted so as to be semi-rigid and to hold the heavy metal in an exposed position relative to the carrier. This arrangement is also adapted to maintain the heavy metal in a substantially exposed and preferably, essentially completely exposed state. These factors combine substantially to avoid chelating, covering or inclusion of the heavy metal by the spacer arm and/or the carrier.

The spacer arm, as characterized above, may be an oligopeptide, an aliphatic compound, or an aliphatic fragment. In the latter two instances, the aliphatic compound or fragment may be covalently bonded to the carrier by means of a Schiff base reaction with an aldehyde group, an amide reaction with an amine or carboxylic acid group using a peptide activator such as carbodiimide, acid chloride and the like, an ester reaction with a hydroxyl or carboxylic acid group using a Schotten Bauman reaction, or azide or acid catalysis reaction, a sulfide reaction using a sulfide coupling agent, or other known coupling reactions for joining organic molecules to proteins. See for example Kabat, E. A., *Structural Concepts In Immunology and Immunochemistry*, 2nd Ed., Holt, Rinenary and Winston, New York, 1976 (a review text of such methods) and Jaime Eyzaguirre, *Chemical Modification of Enzymes: Active Site Studies*, John Wiley & Sons (1982), the disclosures of which are incorporated herein by reference. The oligopeptide, aliphatic compound or fragment will contain backbone groups which provide semi-rigidity to the spacer arm. Preferred groups for developing this semi-rigidity include peptide bonds, olefin bonds, olefinic conjugated systems, ester groups and enone groups. Optionally, and especially where immunogenicity of the heavy metal appears difficult to generate, one or more aromatic rings can be incorporated into the spacer arm to stimulate the development of an immune response.

In general, the oligopeptide spacer arm has the following formula:

—X—(R)—Y wherein X is a coupling group that will bond to the carrier, R is one or more amino acid residues and Y is the Lewis Acid or Base group(s) for heavy metal coordination.

In general, the aliphatic compound or fragment spacer arm has the following formula:

—X—(Q)—Z wherein X is a coupling group that will bond to the carrier, Q is a semirigid aliphatic moiety containing ester, amide, keto, olefin or aromatic groups and the like, and Z is a Lewis acid or Base group(s) for heavy metal coordination.

Preferably, an oligopeptide or aliphatic compound is used as the spacer arm to coordinate a metal cation. In this instance, the pendent Lewis base groups will preferably be positioned at the spacer arm end remote from the carrier. These Lewis base groups function as the coordination site or sites for the metal cation. It is preferable that the deformability of the electron shells of the Lewis base groups and the metal cations be approximately similar. Accordingly, sulfur groups can serve as the Lewis base groups when the metal cations are transition metals or inner transition elements.

The carrier of the immunogen compound is a large biopolymer that is known to participate in the development of hapten antigenicity. Blood serum proteins, amylopectins, polysaccharides, fetal serum components, biologically acceptable natural and synthetic proteins and polyamides such as polyglycine can serve as the carriers. Preferred carriers include serum and tissue proteins. Examples are keyhole limpet hemocyanin (KLH) and bovine serum albumin (BSA). Other examples include ovalbumin and chicken gamma globulin. These carriers have sites for coordinate bonding of the spacer arm. Such sites are preferably populated by amine groups, carboxylic acid groups, aldehyde groups and/or alcohol groups.

Production of Hybridomas

The production of hybridomas according to the invention generally follows the Kohler, Milstein technique. Many heavy metals, however, toxify the mammalian system being used as a source of immune cells. This effect makes it important to determine the highest allowable dose of heavy metal and/or immunogen compound that can be used over a substantially long period of time without killing the host.

Pursuant to the Kohler, Milstein technique, immunization of the mammalian host is accomplished within this dose parameter by subcutaneous or intraperitoneal injection of the immunogen compound in adjuvant. Administration is repeated periodically and preferably for at least four injections. Three days before the spleen is removed, a priming injection of immunogen compound is again administered.

After their separation, the spleen cells are fused with immortal mammal cells such as mouse myeloma cells using the techniques outlined by Kohler and Milstein. Polyethylene glycol (PEG) or electrical stimulation will initiate the fusions.

The fused cells are then cultured in cell wells according to culture techniques known in the art. Cellular secretions in the culture medium are tested after an appropriate time for the presence of the desired cellular products.

Selection Technique

The selection technique for identifying the appropriate monoclonal antibody is an important aspect for determining the immunospecificity desired according to the invention.

The selection techniques according to the invention call for determining, the binding affinity of the hybridoma cellular products against the heavy metal and against cross-reactive controls. In particular, hybridoma culture fluid is tested in screening assays against the heavy metal, the carrier, the carrier-spacer arm product and the immunogen compound as well as optionally against the spacer arm-heavy metal coordinate. Screening assays can be performed by immunoenzymatic-assay, immunofluorescence, fluorescence-activated cell sorter, radioimmunoassay, immunoprecipitative assay or inhibition of biological activity.

The hybridoma cultures selected will exhibit strong binding characteristics to the heavy metal (and immunogen compound) and will not bind with the spacer arm-carrier product and with the carrier itself.

Following the identification of cell cultures producing the desired monoclonal antibodies, subcloning to refine the selected culture can be performed. These techniques are known to those skilled in the art. See for example Goding, James Goding, *Monoclonal Antibodies: Principles and Practice*, 2nd Edition, Academic Press, San Diego, Calif. 1986, the disclosure of which is incorporated herein by reference. Briefly, the appropriately selected cell culture is separated into one cell units which are then recultured. The subclone cultures are then again tested for specific immunoreactivity, lack of cross-reactivity and the amount of monoclonal antibody secreted. Those subcultures exhibiting the highest amounts of secreted monoclonal antibody are chosen for subsequent pilot development.

Following the foregoing techniques, a number of hybridomas producing monoclonal antibodies to mercury cations have been developed. These perpetual cell lines, designated 1F10, 4A10, 1C11, 5GH, 23F8, 2D5 and 5B6 are maintained in culture medium and in frozen medium at liquid nitrogen temperature at the laboratories of Bionebraska.

The immunogenic host for these hybridomas was the BALB/c mouse and the fusion partner was chosen from the mouse myeloma cell lines P3X63-Ag8.653 or SP2/0. Immunizations were accomplished with the immunogen compound formed from KLH, glutathione and mercuric cation functioning as the heavy metal in complete Freund's adjuvant.

PCR Amplification

PCR amplification of Fd and κ regions from the spleen mRNA of a mouse immunized with BSA-glutathione-mercuric ion may be performed as described by Sastry et al., *Proc. Natl. Acad. Sci U.S.A.*, 86, 5728 (1989). The PCR amplification is performed with cDNA obtained by the reverse transcription of the mRNA with primer specific for amplification of heavy chain sequences or light chain sequences.

The PCR amplification of messenger RNA (mRNA) isolated from spleen cells or hybridomas with oligonucleotides that incorporate restriction sites into the ends of the amplified product may be used to clone and express heavy chain sequences (e.g., the amplification of the Fd fragment) and κ light chain sequences from mouse spleen cells. The oligonucleotide primers, which are analogous to those that have been successfully used for amplification of $V_H$ sequences (see Sastry et al., *Proc. Natl. Acad. Sci U.S.A.*, 86, 5728 (1989)), may be used for these amplifications. Restriction endonuclease recognition sequences are typically incorporated into these primers to allow for the cloning of the amplified fragment into a λ phage vector in a predetermined reading frame for expression.

Expression of Fab Fragments on Phage Coat

Phage assembly proceeds via an extrusion-like process through the bacterial membrane. Filamentous phage M13 has a 406-residue minor phage coat protein (cpIII) which is expressed before extrusion and which accumulates on the inner membrane facing into the periplasm of *E. coli*. The two functional properties of cpIII, infectivity and normal (nonpolyphage) morphogenesis have been assigned to roughly the first and second half of the gene. The N-terminal domain of cpIII binds to the F' pili, allowing for infection of *E. coli*, whereas the membrane-bound C-terminal domain, P198-S406, serves the morphogenic role of capping the trailing end of the filament according to the vectorial polymerization model.

A phagemid vector may be constructed to fuse the antibody Fd chain with the C-terminal domain of cpIII (see Barbas et al., *Proc. Natl. Acad. Sci. USA*, 88, 7978 (1991)). A flexible five-amino acid tether (GGGGS), which lacks an ordered secondary structure, may be juxtaposed between the expressed Fab and cpIII domains to minimize interaction. The phagemid vector may also be constructed to include a nucleotide coding for the light chain of a Fab fragment. The cpIII/Fd fragment fusion protein and the light chain protein may be placed under control of separate lac promoter/operator sequences and directed to the periplasmic space by pelB leader sequences for functional assembly on the membrane. Inclusion of the phage F1 intergenic region in the vector. allows for packaging of single-stranded phagemid with the aid of helper phage. The use of helper phage superinfection may result in expression of two forms of cpIII. Consequently, normal phage morphogenesis may be perturbed by competition between the cpIII/Fd fragment fusion protein and the native cpIII of the helper phage for incorporation into the virion. The resulting packaged phagemid may carry native cpIII, which is necessary for infection, and the fusion protein including the Fab fragment, which may be displayed for interaction with an antigen and used for selection. Fusion at the C-terminal domain of cpIII is necessitated by the phagemid approach because fusion with the infective N-terminal domain would render the host cell resistant to infection. The result is a phage displaying antibody combining sites ("Phabs"). The antibody combining sites, such as Fab fragments, are displayed on the phage coat. This technique may be used to produce Phabs which display recombinantly produced Fab fragments, such as recombinantly produced Fab fragments that immunoreact with a mercury cation, on the phage coat of a filamentous phage such as M13.

A phagemid vector (pComb 3) which allows the display of antibody Fab fragments on the surface of filamentous phage, has been described (see Barbas et al., *Proc. Natl. Acad. Sci. USA*, 88, 7978 (1991). Xho I and Spe I sites for cloning PCR-amplified heavy-chain Fd sequences are included in pComb 3. Sac I and Xba I sites are also provided for cloning PCR-amplified antibody light chains. These cloning sites are compatible with known mouse and human PCR primers (see, e.g., Huse et al., *Science*, 246, 1275–1281 (1989)). The nucleotide sequences of the pelB leader sequences are recruited from the λ HC2 and λ LC2 constructs described in Huse et al, ibid, with reading frames maintained. Digestion of pComb 3, encoding a selected Fab, with Spe I and Nhe I permit the removal of the gene III fragment, which includes the nucleotide sequences coding for the antibody Fab fragments. Because Spe I and Nhe I produce compatible cohesive ends, the digested vector may also be religated to yield a phagemid that produces soluble Fab.

Phabs may be produced by overnight infection of phagemid containing cells (e.g., infected *E. coli* XL-1 Blue) yielding typical titers of $10^{11}$ cfu/ml. By using phagemids encoding different antibiotic resistances, ratios of clonally distinct phage may easily be determined by titering on selective plates. In single-pass enrichment experiments, clonally mixed phage may be incubated with an antigen-coated plate. Nonspecific phage will be removed by washing, and bound phage may then be eluted with acid and isolated.

Methods of Application

According to the invention, the metal binding polypeptide can be used to advantage for detection, neutralization, addition or removal of heavy metals from biological or inanimate systems. These methods apply to qualitative and quantitative analyses of minute concentrations of toxic metal cations, in aqueous liquid systems, in biological or environmental systems or in such compositions as perfumes, cosmetics, pharmaceuticals, health care products, skin treatment products, pesticides, herbicides, solvents used in the production of semi-conductor and integrated circuit components and production materials for electronic components. In each application, the presence of minute quantities of metallic cations could constitute deleterious contaminants. Their ready and early detection will avoid later production or regulatory set-backs.

Alternatively, the presence of minute quantities of heavy metals in certain instances may be desirable. For example, the presence of inorganic moieties in such mixtures as doping materials for semi-conductors and integrated circuits contributes to the properties of the product. Quality control of the presence and concentration of these heavy metals is essential for the functioning of the product. The detection methods of the invention enable ready and early measurement of the presence of such heavy metals and avoid later production or regulatory difficulties.

Heavy metals in biological or inanimate systems can also be removed by methods according to the invention. In the main, immobilization of the metal binding polypeptides on a solid support followed by its mixture with the materials of the biological or inanimate system will remove the heavy metals. In this instance, the immobilization of the monoclonal antibodies can be accomplished by techniques known to those of skill in the art. See, for example, *Affinity Chromatography*, C. R. Fowe & P. D. G. Sean, John Wiley & Sons, London 1974, the disclosure of which is incorporated herein by reference. Removal is accomplished by passing a fluid mixture of the system ingredients suspected as having the heavy metals over the immobilized metal binding polypeptides. Of course, the metal binding polypeptides are designed to be specific for the heavy metal sought to be removed.

An advantage of this method is the removal of undesirable heavy metals in the presence of similarly structured desirable metal species. For example, whole blood from a patient suffering from mercury poisoning can be removed from the patient, optionally filtered to return the cellular blood components to the patient, and the serum or blood passed over immobilized metal binding polypeptides specific for the mercury. The purified serum or blood can then be returned to the patient. The mercury will be removed but other blood serum components such as zinc, calcium, iron and the like will not.

Likewise, a doping mixture for integrated circuits which contains a trace transition metal can be passed over immobilized metal binding polypeptides which are specific for an undesirable neighboring transition metal. The complexation will remove any of the undesirable transition metal present and produce an ultrapure doping mixture for the integrated circuit components.

Methods for adding heavy metals to biological or inanimate systems focus on the delivery of the heavy metal to a particular site. In this instance, the metal binding polypeptides will be bifunctional. The second binding site will be adapted to complex with a selected site within the biological or inanimate system. In this fashion, the metal binding polypeptide-heavy metal conjugate will deliver the heavy metal to a specific site.

This method is particularly suited for heterogenous delivery processes. These processes enable the non-uniform concentration of the heavy metal in a system that would otherwise cause its uniform or homogenous distribution. Examples include the delivery of radioactive compounds to specific organs and/or tissues in biological or inanimate systems and the delivery of metallic cations molecules to specific sites within a system. Fluid or semi-fluid flow of system ingredients would be preferred so that transport of the metal binding polypeptide-heavy metal conjugate can be rapidly made. The presence of a fluid medium, however, is not an important characteristic. Gels, semi-solidified systems and the like can be employed as long as some semi-fluid connection is present for diffusion of heavy metal and metal binding polypeptide. For administration of the metal binding polypeptides to biological systems, the antigenicity of the metal binding polypeptides themselves will preferably be minimized. Use of species-specific cell sources for generation of the hybridomas is an appropriate technique for minimizing the antigenicity of metal binding polypeptides, such as monoclonal antibodies. Cross-reaction studies of the host and the metal binding polypeptide can also be made to determine lack or minimization of metal binding polypeptide sensitivity. A preferred means for avoiding adverse immune reaction is the use of the Fab or $F(ab)_2$ fragments of the monoclonal antibodies of this invention. These fragments do not contain the heavy chain tail primarily responsible for such immune reactions and are made by known methods. Their small size and direct carriage of the heavy metal allows them easily to pass through or intimately to attach to cellular membrane. They have few bulky groups that would interfere with these processes.

In instances involving in vivo application, the dosage level and routes of monoclonal antibody administration will follow the judgment of the medical practitioner who is in an appropriate position to understand the needs and problems of the patient or mammal. In these situations, the dosage levels of monoclonal antibody compositions being administered will be consonant with the toxicity and sensitivity levels determined for the patient or mammal. The monoclonal antibody compositions will generally be combined for administration with a pharmaceutically acceptable medium such as water, alcohol, buffered aqueous medium, excipients, diluents and the like. Active transport agents can also be included. In general, the processes of administration for removal or addition of heavy metals will maintain concentrations as high as possible so that the period for patient intervention is minimized. In each instance, consideration of the physiological characteristics of the heavy metal will be important for determining the dosage levels and route of administration.

Specific Applications

A particular application of the present invention contemplates a method for the production of monoclonal antibodies specific for the mercuric cation or another toxic, heavy metal cation. In accordance with this method, the heavy metal cation in question is combined into an immunogen compound as described above and suspended in an aqueous medium. The preferred protein carrier for the immunogen compound in this instance is keyhole limpet hemocyanin. The preferred spacer arm in this instance is an oligopeptide which has sulfhydryl groups capable of coordinating with the heavy metal cation. Glutathione is especially preferred as the spacer arm. The suspension of immunogen compound is used to immunize a host mammal such as a mouse following the techniques outlined above. The laboratory strain of mouse designated BALB/c is particularly preferred.

Antibody-producing cells of the immunized host's spleen are collected and converted into a suspension. These spleen cells are fused with immortal cells as described above. Preferably, myeloma cells of the same animal species as the immunized host are used as the fusion partner. Typically, a cell fusion promoter such as polyethylene glycol is employed to cause formation of the hybridoma cells. The hybridoma cells are diluted and cultured in a medium which does not allow for the growth of unfused cells.

The monoclonal antibodies produced and secreted by the hybridomas are thereafter assayed for the ability to bind immunologically with the heavy metal cations used for immunization. They are further selected for lack of cross-reactivity with carrier and with carrier-spacer arm. The preferred assay method in this context is an enzyme-linked immunosorbent assay.

The resulting monoclonal antibodies are specific for toxic heavy metal cations and exhibit strong complexation to the heavy metal cations when in the presence of spacer arm, the spacer arm-carrier composition and other similarly structured cations. Preferred monoclonal antibodies are selectively immunoreactive with cations of mercury.

According to an embodiment of a method for detecting the presence of toxic heavy metal cations, an immobilized coordinating compound is combined with the unknown mixture containing the toxic heavy metal cation. The heavy metal cation complexes with coordinating compound and is immobilized thereto. Removal of the non-immobilized components leaves a mixture of the immobilized toxic heavy metal cation. Addition of the metal binding polypeptide, specific for the toxic heavy metal cation forms an immobilized cation-metal binding polypeptide conjugate. Its presence and concentration can be assayed by an ELISA technique or other tagging or visualization technique known to those of skill in the art. In this process, of course, non-immobilized metal binding polypeptide is removed before the assay is conducted.

A kit for quantitatively measuring the presence of a heavy metal cation by the method described above is a further aspect of the invention. The kit will include the immobilized coordination compound, preferably, attached to a solid support such as the well of a microtiter plate or a chromatographic material, and a metal binding polypeptide specific for the toxic metal cation in question, wherein the metal binding polypeptide is preferably metered into several aliquots of varying, known concentration. A third component of the kit will be the visualization or tagging assay material for determination of the presence of the metal binding polypeptide-heavy metal cation conjugate. If desired, a meter or other device for detecting and signaling the level of visual or other reading from the assay may also be included.

The invention will be further characterized by the following examples. These examples are not meant to limit the scope of the invention which has been fully set forth in the foregoing description. Variation within the concepts of the invention are apparent to those skilled in the art.

EXAMPLE 1

Mercury Cation Monoclonal Antibodies

A. General Procedures

1. Generation of Hybridomas

Hybridoma antibodies have been produced with the spleen cells of BALB/c mouse that had received multiple injections of mercuric ions reacted with glutathione to produce a mercuric ion coordinate covaelent compound, which was covalently bound to keyhole limpet hemocyanin ("KLH"). The KLH in complete Freund's adjuvant was utilized to assist in the elicitation of an immune response in the host animal. Glutathione is a three amino acid residue peptide having one reactive sulfhydryl group which forms a coordinate bond with mercuric ions.

Of hybridomas isolated, a number were determined to be producing monoclonal antibody specific for glutathione as set forth below in Table I. In addition, eight other hybridomas (1F10, 4A10, 1C11, 5G4, 23F8, 2D5, 5B6 and 3E8) were producing monoclonal antibodies that were strongly positive against glutathione-mercuric ions but negative against glutathione without mercuric ions (Tables I and II). These three antibodies were subcloned by limiting dilution for further characterization. Another antibody (3F5), not included in the Tables, which appeared to be specific for glutathione but bound more tightly in the presence of mercuric ions, was also subcloned.

TABLE I

ELISA Results From Initial Screening of Hybridoma Antibodies Reactive With Glutathione or Glutathione-Mercuric ions

| Hybridoma | Glutathione | Glutathione-mercuric ions |
| --- | --- | --- |
| 1H11 | 1.202 | 1.246 |
| 2A9 | 1.052 | 0.758 |
| 3A12 | 2.127 | 1.792 |
| 3H9 | 2.134 | 1.606 |
| 1F10 | 0.406 | 1.175 |
| 3E8 | 0.410 | 1.075 |
| 4A10 | 0.400 | 1.104 |
| Negative[b] | 0.456 | 0.428 |

[a]Values are the absorbance at 405 nm shown by the specified hybridoma antibody in the ELISA.
[b]The value shown is the average absorbance at 405 nm of six wells on and ELISA plate that received culture fluid containing a monoclonal hybridoma antibody specific for dinitrophenol instead of culture fluid containing a mercuric ion specific monoclonal antibody in the first step of the assay.

ELISA Results of Hybridoma Antibodies Immunoreactive With Glutathione-Mercuric Ions Ninety-six-well microtiter plates (EIA/RIA grade) were treated with BSA-glutathione, blocked with 1% polyvinyl alcohol in PBS and used for the ELISA. One hundred microliters of mercuric nitrate 100 ppb in Hepes 100 mMolar pH 7.2-was added to the wells for 30 minutes. The plates were washed three times, and then hybridoma culture supernatant was added for 30 minutes at room temperature, followed by goat anti-mouse conjugated to horseradish peroxidase. After incubation for 30 minutes at room temperature, the plates were washed, and 100 ul of ABTS peroxidase substrate was:added to each well. After 15 min at room temperature-the absorbance of each well was read at 405 nanometers. The results are shown in Table II.

TABLE II

Reactivity of
Antibodies with Glutathione-Mercuric Ions by ELISA

| Antibody | BSA-GSH-HgCl | BSA-GSH | Isotype |
| --- | --- | --- | --- |
| 1C11 | 0.458 | 0.094 | IgM |
| 1F10 | 0.550 | 0.092 | IgA |
| 2D5 | 0.818 | 0.090 | $IgG_1$ |
| 4A10 | 0.636 | 0.078 | IgM |
| 5B6 | 0.738 | 0.019 | $IgG_3$ |
| 5G4 | 0.313 | 0.028 | $IgG_1$ |
| 23F8 | 1.134 | 0.168 | IgM |

Only one positive subclone was obtained from hybridoma 3E8, and it subsequently lost its antibody-secreting ability. Several subclones secreting antibodies that were specific for mercuric ion were isolated from the 1F10 and 4A10 mercuric ion-specific hybridomas. The results of the analysis of these subclones and those from 3F5 with BSA-glutathione-mercuric ion and BSA-glutathione are shown in Table III. All of the frozen hybridoma samples have been thawed from liquid nitrogen and assayed for persistence of antibody secretion after thawing.

TABLE III

ELISA Results from Hybridoma
Subclones Specific for Glutathione
or Glutathione-Mercuric ions

| Hybridoma | Glutathione | Glutathione-mercuric ion |
| --- | --- | --- |
| 1F10.A6 | 0.289 | 1.048 |
| 1F10.A9 | 0.300 | 0.979 |
| 1F10.A11 | 0.285 | 1.015 |
| 1F10.B1 | 0.302 | 0.861 |
| 1F10.B2 | 0.271 | 0.952 |
| 1F10.E2 | 0.292 | 1.005 |
| 4A10.B4 | 0.322 | 1.279 |
| 3F5.A8 | 0.494 | 0.773 |
| 3F5.B11 | 0.563 | 0.865 |
| 3F5.D5 | 0.658 | 0.884 |
| Negative[b] | 0.332 | 0.295 |

[a]Values are the averages of the absorbance at 405 nm of triplicate samples for each hybridoma subclone in an ELISA.
[b]The value shown is the average absorbance at 405 nm for six wells in an ELISA plate that received culture fluid containing a monoclonal hybridoma antibody specific for dinitrophenol instead of culture fluid containing a mercuric ion-specific monoclonal antibody in the first step of the assay.

Based on this ELISA assay work, hybridomas 1F10 and 4A10 were further evaluated to determine if the antibodies secreted were specific for mercuric ions.

2. Determination of Mercuric-ion Specific Monoclonal Antibodies

Various methods were used to confirm that the antibodies secreted by hybridomas 4A10 and 1F10 were specific to mercuric ions. If the antibody being secreted by these hybridomas were specific, it should be possible to inhibit binding of the antibody to glutathione-mercuric ions by incubation in the presence of various concentrations of mercuric chloride. This competitive inhibition assay was conducted with antibody-containing culture fluids from the parental hybridomas 4A10 and 1F10. The results for inhibition of 1F10 by mercuric chloride and magnesium chloride are shown in FIG. 1.

FIG. 1 shows inhibition of binding of antibody secreted by hybridoma designated as 1F10 to immobilized glutathione-mercuric ion by various concentrations of mercuric ions. Metal ions at the indicated concentrations were incubated with culture fluid from the monoclonal antibody in an enzyme-linked immunosorbent assay ("ELISA") plate. The absorbance at 405 nm was determined for each sample, and the percent inhibition of each metal ion concentration was determined by the following formula:

$$\text{Percent inhibition} = \frac{A_{405} \text{ of inhibitor} - A_{405} \text{ of neg. control}}{A_{405} \text{ of pos. control} - A_{405} \text{ of neg. control}}$$

Magnesium chloride at the same concentrations as mercuric chloride was included as a control to rule out the possibility that inhibition could be due to excess amounts of divalent cations or increased ionic strength of the incubation solution. It can be seen that 50% inhibition with mercuric chloride occurs between 0.0001 and 0.00001 M, while magnesium chloride approaches 50% inhibition only at the highest concentration.

Therefore, in both enzyme-linked immunosorbent assay (ELISA) and the competitive assay, the monoclonal antibodies were specific for mercuric ions. The preformation of a mercuric ion coordinate covalent complex is not a requirement for monoclonal antibody recognition of mercuric ion. Thus, the monoclonal antibody reacts with free mercuric ions which are independent of coordinating agents.

Figure 2:
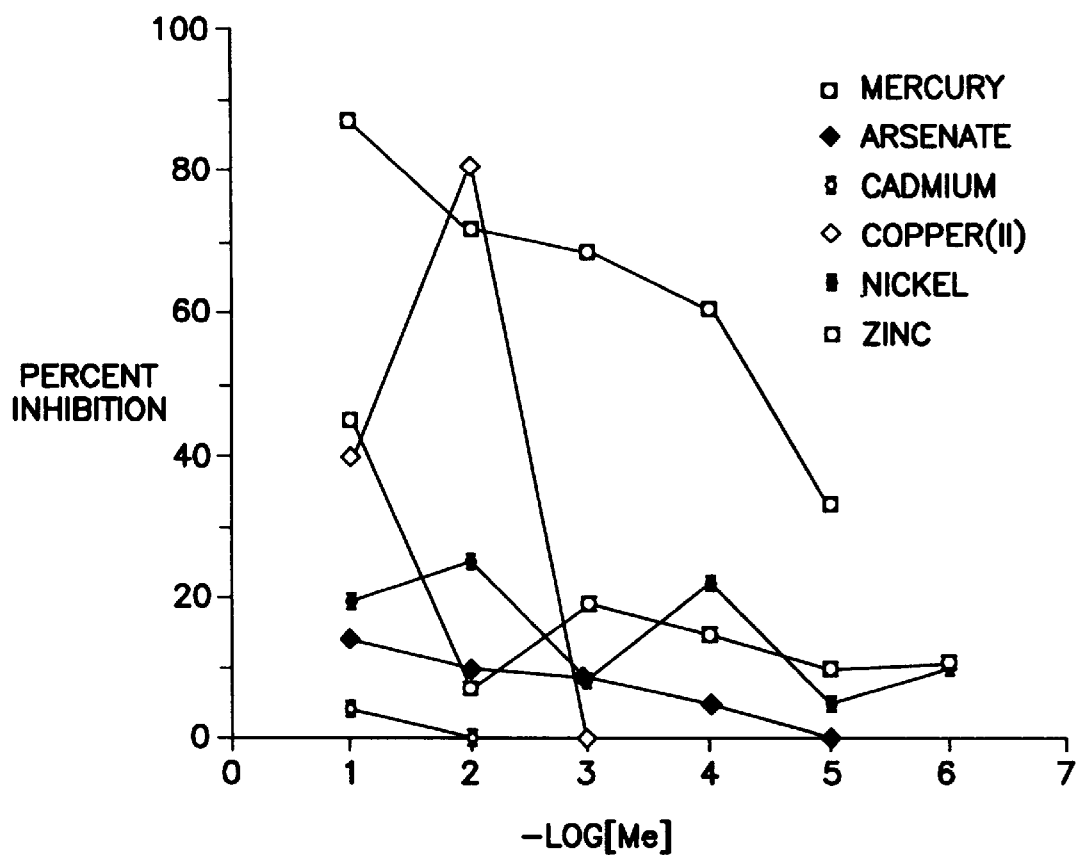
FIG. 2 shows a graph of an immunosorbent assay. The results depict the competitive inhibitory binding of mercury and various divalent cations for a monoclonal antibody to mercury.

Various other metals were assayed for inhibition of binding of the monoclonal antibodies to mercuric ion. The cationic metals assayed include the ions of zinc, copper, cadmium, nickel, and arsenic. The results of these inhibition assays are shown in FIG. 2. To produce these results the binding of monoclonal antibody secreted by the hybridoma designated as 1F10 to immobilized glutathione-mercuric ions by various concentrations of divalent cations was examined. Metal ions at the indicated concentrations were incubated with culture fluid from the antibody in an ELISA plate. The absorbance at 405 nm was determined for each sample, and the percent inhibition of each metal ion concentration was determined by the same formula used for FIG. 1.

However, none of the metals showed a titratable inhibition of monoclonal antibody binding similar to that seen with free mercuric ions. Therefore, based upon the heavy metal ions tested, the monoclonal antibodies produced by immunization with mercuric ions are specific for mercuric ions.

Further analysis shows that the monoclonal antibodies produced are specific for the mercuric ions per se and that glutathione is not needed for the monoclonal antibodies to react with and bind to the mercuric ions. The monoclonal antibody from hybridoma 1F10 was assayed against BSA-glutathione, BSA-glutathione mercuric ions, and BSA-mercuric ions. When compared against a negative control consisting of a monoclonal antibody specific for an unrelated antigen the results show that the monoclonal antibody binds to mercuric ion in the absence of glutathione.

BSA-glutathione adsorbed to the wells of a microliter plate effectively binds mercuric ions from solution and enables detection of mercuric ions in a concentration as low as $10^{-9}$ M (0.2 ppb) by the antibody (Table IV) without appreciable loss of sensitivity.

TABLE IV

Assay Utilizing BSA-Glutathione
Added to Polyvinyl Chloride Microtiter Plates

| Hg Conc. (M)[a] | A405 |
|---|---|
| $10^{-1}$[b] | 0.442 |
| $10^{-2}$ | 1.213 |
| $10^{-3}$ | 1.453 |
| $10^{-4}$ | 0.936 |
| $10^{-5}$ | 1.364 |
| $10^{-6}$ | 0.962 |
| $10^{-7}$ | 1.113 |
| $10^{-8}$ | 1.113 |
| $10^{-9}$ | 1.107 |
| 0 | 0.394 |

[a]Mercuric ion concentration refers to the concentration of mercuric chloride in the PBS added to the well to which BSA-glutathione had been absorbed.
[b]The absorbance at concentrations of $10^{-1}$ M is only slightly higher than the control because the large numbers of ions present creates a substantial amount of stearic hindrance which prevents binding and is not evidence of any lack of specificity of the monoclonal antibody.

Figure 3:
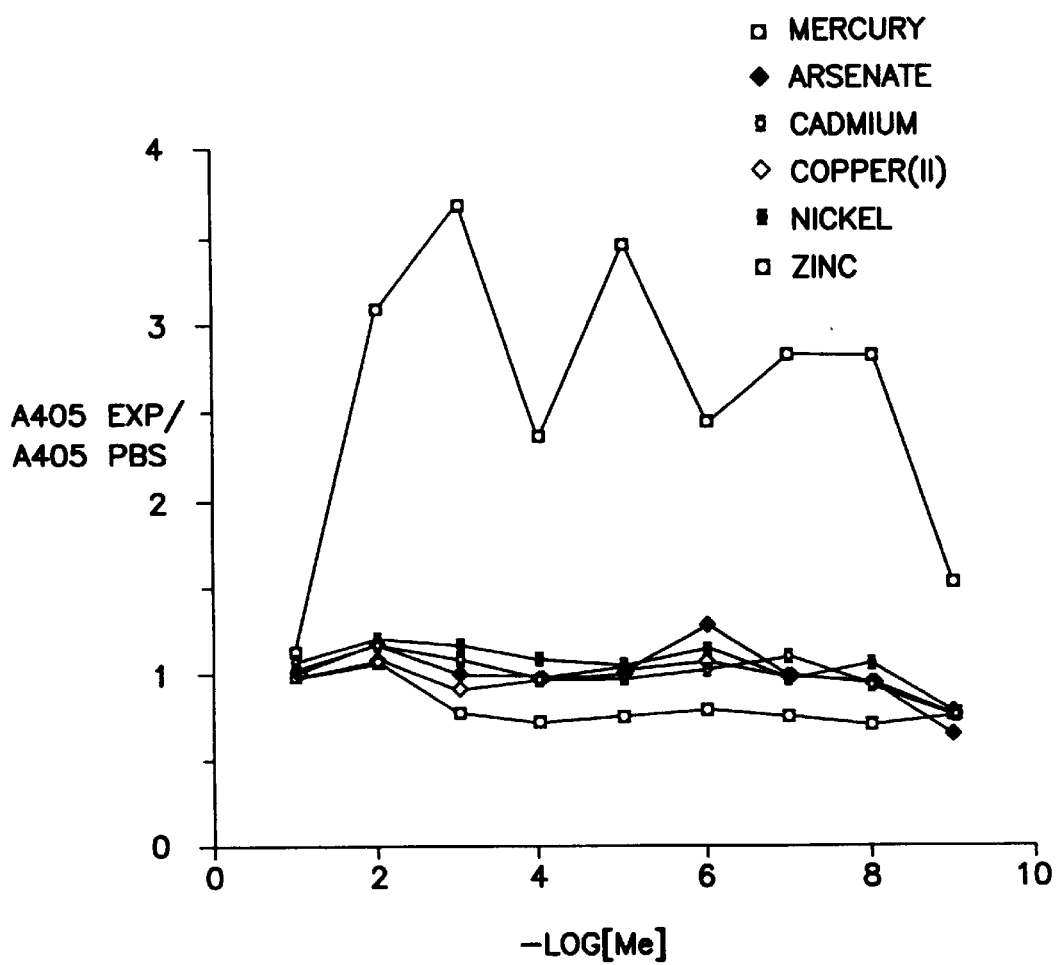
FIG. 3 is a graph of the results of an immunosorbent assay of the binding of a monoclonal antibody to several heavy metal ions. The monoclonal antibody is specific for mercuric cations.

The specificity of the antibody reactivity for mercuric ion is shown in FIG. 3. Here the reactions of various coordinated heavy metal ions with the monoclonal antibody secreted by the hybridoma designated 1F10 indicate that it is specific for mercuric ions.

Phosphate-buffered saline ("PBS") containing metal ions at the indicated concentrations was added to triplicate microtiter wells to which BSA-glutathione had been absorbed. After incubation at room temperature for 30 minutes, the plates were washed to remove unbound metals, and the plates were used for the standard ELISA to detect mercuric ions. In this experiment various heavy metal ions at the indicated concentrations were added to microtiter plates to which BSA-glutathione had been adsorbed. The PBS containing the metal ions was allowed to incubate at room temperature for 30 minutes, and the plates were then used in an ELISA to determine whether the monoclonal antibody would react with the bound metal. The data in FIG. 3 show that mercuric ion is the only heavy metal ion which demonstrates a reasonable increase in absorbance.

B. Particular Preparations

1. Linkage of Mercuric Ions to Protein Carriers

To prepare antigen for injection and immunoassay, 136 mg $HgCl_2$ (400 umoles), 61 mg glutathione (200 umoles) and 54 mg NaCl were dissolved in 10 ml of water. Thirty milliliters of cold ethanol were added and incubated for 30 minutes at 0° C. The reaction mixture was centrifuged at 10,000 for 30 minutes, and the pellet was washed with 30 ml of cold ethanol. The pellet was dissolved in 200 ml of 40% dimethylformamide pH 4.8, containing 200 mg of 1-ethyl-3-(3-dimethylaminopropyl)-carbodiimide, and 1 g of either bovine serum albumini or keyhole limpet hemocyanin were added to the solution. The reaction mixture was stirred at room temperature overnight. The mixture was then centrifuged as above, resuspended in PBS, and dialyzed overnight at 4° C. against 4 liters of PBS.

2. Immunization of BALB/c Mice

BALB/c mice received multiple injections of the antigen prepared with 10 ug of protein per injection. The antigen was mercuric ion-glutathione-KLH emulsified in Freund's adjuvant. Complete adjuvant was used for the first two injections, while incomplete adjuvant was used for all subsequent injections. After the fourth injection, a drop of blood from the tail of each mouse was collected separately in 0.5 ml of PBS, and each sample was assayed by ELISA for the presence of antigen-specific antibody. The mice used for hybridoma production received an intraperitoneal injection consisting of 10 ug of antigen in PBS 3-4 days before cell fusion.

3. Hybridoma Production

The spleen was removed aseptically from a mouse, and the cells were isolated by placing the spleen in 5 ml of sterile PBS and teasing it with two sterile, 18-gauge hypodermic needles. The cell suspension was added to an empty sterile, conical, 15-ml centrifuge tube and tissue fragments-were allowed to settle for 1-2 minutes. The cells still in suspension were placed in a tube similar to that above and centrifuged at 300 g for 10 minutes at room temperature. The cells were then washed 3 times by centrifugation in serum-free DMEM-(Dulbecco's modified Eagle's medium). Spleen cells were co-pelleted with P3X63-Ag8.653 myeloma cells at a ratio of 4 spleen cells to 1 myeloma cell. The supernatant fluid was removed, and the pellet was suspended in 1 ml of 35% polyethylene glycol for 1 minute. The polyethylene glycol was gradually diluted by addition of increasing amounts of serum-free DMEM over a period of 15 minutes. The cells were then suspended in HAT medium (Monoclonal Antibodies, Kennett, McKean, Backitt, eds. Plenum press 1981) at a concentration of $2 \times 10^5$ myeloma cells per ml, and 4 drops from a 5-ml pipet were added to each well of 5 96-well microtiter plates. The plates were incubated in 10% $CO_2$ at 37° C. for one week. At that time half of the culture fluid was withdrawn from each well and replaced by 2 drops of fresh HT medium (HAT medium without aminopterin), and the plates were incubated as above for another week. Then, approximately 100 ul of culture fluid was taken from each well containing macroscopically visible cell growth, and the ELISA technique described infra was used for identification of those culture fluids containing mercuric ion-specific antibodies.

4. Enzyme-Linked Immunosorbent Assay (ELISA)

Polyvinyl chloride microtiter assay plates were coated with antigen by addition of 50 ul of mercuric ion-glutathione-BSA or glutathione-BSA at a concentration of 5 ug/ml in PBS to each well of the plate. The plates were allowed to incubate at room temperature overnight to allow the antigen to dry on the plate. Next day the plates were blocked by addition of 200 ul of 5% nonfat dry milk in PBS to each well; the addition of the dry milk blocked the remaining protein-binding sites. The plates were incubated for 2 hours at room temperature, then washed 3 times with ELISA wash (PBS with 0.1% of nonidet P-40).

Fifty microliters of culture fluid being assayed for the presence of antigen-specific antibody were added to the appropriate well, and the plates were incubated at room temperature for 2 hours. The plates were again washed 3 times with ELISA wash, and 50 ul of goat anti-mouse serum (Cooper Biomedical) diluted 1:1000 in 2% BSA in PBS were added to each well. After incubation and washing as above, 50 ul of rabbit anti-goat serum conjugated to alkaline phosphatase (Sigma) diluted 1:1000 in 50 mM Tris-HCl, pH 8.0, containing 1 mM $MgCl_2$, 5% BSA and 0.04% $NaN_3$, were added to each well. After being incubated and washed as above, 150 ul of phosphatase substrate (0.4 mM dinitrophenol phosphate in 1 M diethanolamine, pH 9.8, containing 25 mM $MgCl_2$) were added to each well.

The enzyme catalyzed conversion of dinitrophenol phosphate to dinitrophenol was allowed to proceed at room temperature for 30–60 minutes. The absorbance of each well at 405 nm (dinitrophenol) was measured with a UV spectrometer.

The use of other enzymes as sensors is also possible provided that such enzymes can be linked to an appropriate antibody, and catalyze a reaction which produces a color change. For example, beta galactosidase, urease, or horseradish peroxidase could be utilized in this context.

5. Inhibition of Binding of Mercuric ion-Specific Antibody by Metals

Microtiter assay plates containing mercuric ion-glutathione-BSA were prepared as described above. After blocking the plates with non-fat dry milk, 25 ul of a solution containing a known concentration of the metal to be assayed were added, to each of triplicte wells of the plate, along with 25 ul of culture fluid containing mercury-specific antibody. The concentrations of metal ranged from $2 \times 10^{-1}$ M to $2 \times 10^{-6}$ M, so the final concentration of metal in the wells ranged from $10^{-1}$ M to $10^{-6}$ M. The plates were incubated for 30 minutes at room temperature, washed with ELISA wash as above, and then assayed using the ELISA technique as described above. The absorbance at 405 nm was measured for each well, and the percent inhibition of antibody binding for each concentration of metal was calculated according to the following formula:

$$\text{Percent inhibition} = \frac{A_{405} \text{ of inhibitor} - A_{405} \text{ of neg. control}}{A_{405} \text{ of pos. control} - A_{405} \text{ of neg. control}}$$

The negative control measured the binding of a dinitrophenol specific antibody to the antigen mentioned above in the presence of the corresponding metal ions. The positive control consisted of triplicate wells that contained 25 ul of mercuric ion-specific antibody and 25 ul of PBS with no metal.

6. Binding of Mercuric ions to Immobilized Coordinating Spacer Arms

One hundred microliters of BSA-glutathione at a concentration of 5 ug/ml were added to the wells of a microtiter plate and allowed to dry overnight. The plates were then blocked with nonfat dry milk as above. One hundred microliters of PBS containing a known concentration of the metal ion to be assayed were added to triplicate wells on the plate, which was then incubated at room temperature for 30 minutes. After this incubation period the plates were washed with ELISA wash to remove unbound metal ions and then used in the standard ELISA to measure reactivity with the mercuric ion-specific antibody.

7. Assay of Mercuric Ion-Specific Antibody Against BSA Glutathione, BSA Glutathione-Mercury and BSA-Mercury Mercuric ion specific antibody secreted from hybridoma 1F10 was assayed against BSA-glutathione, BSA-glutathione-mercury and BSA-mercuric ions. The results set forth below are the average absorbance plus the standard deviation of nine individual samples assayed against the three antigens.

| Antigen | 1F10.A11 | Neg. Control |
|---|---|---|
| BSA-glutathione | 0.418 ± 0.014 | 0.419 ± 0.061 |
| BSA-glutathione-mercuric ion | 3.144 ± 0.132 | 0.171 ± 0.042 |
| BSA-mercuric ion | 2.861 ± 0.092 | 0.223 ± 0.027 |

EXAMPLE 2

Nucleotides Coding for Heavy Chain Fd Fragments and Light Chains from Mercury Cation Monoclonal Antibodies Synthesis of Nucleotides Encoding the Heavy and Light Chain Variable Regions of the Mercury-Cation Antibodies RNA was isolated from hybridoma cells with guanidine isothiocyanate (Evans et al., *BioTechniques*, 8, 357 (1990)), and enriched for poly(A)+RNA by passage over a poly(dT)-cellulose column (Aviv et al., *Proc. Natl. Acad. Sci. USA*, 69, 1408 (1972)). First-strand cDNA synthesis was catalyzed by MuLv reverse transcriptase with a Promega RiboClone kit, according to the manufacturer's directions. The primers used for cDNA synthesis were complementary to the 5' end of the $C_H1$ domain of the heavy chain expressed by the hybridoma of interest, or to the 5' end of the Cκ domain. The primers used for cDNA synthesis are shown in Tables V and VI. The κ-chain primer contained an XbaI site at its 5' end, while all the heavy chain primers contained an SpeI site at their 5' ends. The κ-chain primer encoded residues 107–111 of the constant region domain; the μ-chain primer encoded residues 116–120 of the $C_H1$ domain; the $\gamma_1$-chain primer encoded residues 122–126 of the $C_H1$ domain; and the $\gamma_3$-primer encoded residues 117–121 of the $C_H1$ domain.

Amplification of Antibody Variable Regions by Polymerase Chain Reaction

The primer used for cDNA synthesis of the variable region of a particular antibody polypeptide chain was also used for PCR amplification of that variable region, in conjunction with an appropriate V-region primer as described in Huse et al., *Science*, 246, 1275 (1989). In addition, the $V_H$ primer 5'-AGGTCCAACTGCTCGAGTCTGG-3' was used to amplify the mAb 2D5 and 5B6 heavy chains. The PCR was performed as described in Sastry et al, *Proc. Natl. Acad. Sci. USA*, 86, 5728 (1989).

TABLE V

Primers Used for cDNA Synthesis and/or PCR Amplification

| | Light chain | | Heavy chain | |
|---|---|---|---|---|
| Antibody | Reverse | Forward | Reverse | Forward |
| 2D5 (γ1,κ) | 33615 | SS119 | 438 | SS131 |
| 4A10 (μ,κ) | 33615 | SS92 | 65656 | SS131 |
| 1F10 (α,κ) | 33615 | SS119 | — | — |
| 5G4 (γ3,κ) | 33615 | SS119 | 438 | SS131 |
| 5B6 (γ3,κ) | 33615 | SS119 | 2034 | VhA |
| 1C11 (μ,κ) | 33615 | SS119 | 65656 | SS131 |
| 23F8 (μ,κ) | 33615 | SS119 | 65656 | SS131 |

TABLE VI

Sequences of Primers Used for cDNA Synthesis and/or PCR Amplification

| Primer | Primer Sequence | |
|---|---|---|
| 2034 | 5'- GCC AGT GAT CAA GGG TTA GAC CAG ATG GGG CTG T -3' | (SEQ ID NO:27) |
| 438 | 5'- GGC AGC ACT AGT AGG GGC CAG CAG TGG ATA -3' | (SEQ ID NO:28) |
| SS92 | 5'- CCAGTTCCGA GCTCGATGTT TTGATGACCC AAACTCCAC -3' | (SEQ ID NO:29) |
| 33615 | 5'- gaagatctag acttactatg cagcatcagc -3' | (SEQ ID NO:30) |
| SS119 | 5'- CCAGTTCCGA GCTCGACATC CAGATGACCC AGTCTCCAT -3' | (SEQ ID NO:31) |
| SS131 | 5'- AGGTCCAGCT GCTCGAGGTC CAGCTGCAGC AGT -3' | (SEQ ID NO:32) |
| 65656 | 5'- AGGAGACTAG TGGTTACTAA TTTGGGAAGG ACTG -3' | (SEQ ID NO:33) |
| Vha | 5'- aggtccagct gctcgagtct gg -3' | (SEQ ID NO:34) |

Sequence Determination of Nucleotides Encoding the Heavy and Light Chain Variable Regions of the Mercury Cation Antibodies The PCR amplified nucleotide sequences encoding the heavy and light chain variable regions of the mercury cation antibodies were cloned into Bluescript (Stratagene, La Jolla, Calif.). The sequences of these nucleotides were determined by the dideoxy chain termination method (Sanger et al., Proc. Natl. Acad. Sci. USA, 74, 5463 (1977)). The sequences of at least three PCR products for each heavy and light chain were determined to allow detection of incorporation errors by Taq polymerase. The nucleotide and deduced amino acid sequences of the heavy and light chain variable regions of the mercury-specific antibodies are shown in FIGS. 4A–C and 5A-B.

FIGS. 4A–C depict the nucleotide and deduced amino acid sequences for the heavy chain variable regions of a number of monoclonal antibodies that immunoreact with a mercury cation. The following sequences are shown:

the heavy chain variable region nucleotide acid sequence (SEQ ID NO:1) and deduced amino acid sequence (SEQ ID NO:2) for monoclonal antibody 4A10;

the heavy chain variable region nucleotide sequence (SEQ ID NO:3) and deduced amino acid sequence (SEQ ID NO:4) for monoclonal antibody 1C11;

the heavy chain variable region nucleotide sequence (SEQ ID NO:5) and deduced amino acid sequence (SEQ ID NO:6) for monoclonal antibody 5G4;

the heavy chain variable region nucleotide sequence (SEQ ID NO:7) and deduced amino acid sequence (SEQ ID NO:8) for monoclonal antibody 23F8;

the heavy chain variable region nucleotide sequence (SEQ ID NO:9) and deduced amino acid sequence (SEQ ID NO:10) for monoclonal antibody 2D5; and the heavy chain variable region nucleotide sequence (SEQ ID NO:11) and deduced amino acid sequence (SEQ ID NO:12) for monoclonal antibody 5B6.

FIGS. 5A-B depict the nucleotide and deduced amino acid sequences for the light chain variable regions of a number of monoclonal antibodies which immunoreact with a mercury cation. The following sequences are shown:

the light chain variable region nucleotide sequence (SEQ ID NO:13) and deduced amino acid sequence (SEQ ID NO:14) for monoclonal antibody 1F10;

the light chain variable region nucleotide sequence (SEQ ID NO:15) and deduced amino acid sequence (SEQ ID NO:16) for monoclonal antibody 4A10;

the light chain variable region nucleotide sequence (SEQ ID NO:17) and deduced amino acid sequence (SEQ ID NO:18) for monoclonal antibody 1C11;

the light chain variable region nucleotide sequence (SEQ ID NO:19) and deduced amino acid sequence (SEQ ID NO:20) for monoclonal antibody 5G4;

the light chain variable region nucleotide sequence (SEQ ID NO:21) and deduced amino acid sequence (SEQ ID NO:22) for monoclonal antibody 23F8;

the light chain variable region nucleotide sequence (SEQ ID NO:23) and deduced amino acid sequence (SEQ ID NO:24) for monoclonal antibody 2D5; and the light chain variable region nucleotide sequence (SEQ ID NO:25) and deduced amino acid sequence (SEQ ID NO:26) for monoclonal antibody 5B6.

EXAMPLE 3

Expression of Heavy Chain Fd Fragments and Light Chains from Mercury Cation Monoclonal Antibodies Vector Construction The pelB leader sequences and cloning sites for the heavy-chain fragment and light chain may be derived from phagemids excised from γ Hc2 and γ Lc2 γ vectors as described in Huse, et al., Science, 246, 1275–1281 (1989). The sequences are modified to remove a redundant Sac I site from Hc2 phagemid and a Spe I site from the Lc2 phagemid. The combinatorial phagemid vector pComb is constructed from these two modified phagemids by restricting each with Sca I and EcoRI and combining them in a ligation reaction. Recombinants are screened for the presence of two Not I sites yielding the combinatorial vector pcomb. The tether sequence GGGGS and gIII fragment (gene coding for coat protein III of filamentous phage M13 (see Barbas, et al., Proc. Natl. Acad. Sci. USA, 88, 7978 (1991)) from Spe I to Nhe I are the product of PCR of M13mp18 (Yanisch-Perron, et al., Gene, 33, 103–119 (1985)) using the oligonucleotides 5'-GAGACGACTAGTGGTGGCGGTGGCTCTCCATTCG TTTGTGAATATCAA-3' and 5'-TTACTAGCTAGCATAATAACGG AATACCCAAAAG AACTGG-31' as reported in Barbas, et al., Proc. Natl. Acad. Sci. USA, 88, 7978 (1991).

The lacZ promoter, operator, and Cap-binding site controlling light chain expression are the product of PCR with M13mp18 using oligonucleotides 5'-TATGCTAGCTAGTAACACGACAGGTTTCCCGACTGG-3' and 5'-AGCTTTGAATTCGTGAAATTGTTATCCGCT-3' as reported in Barbas et al., ibid. The PCR fragments encoding the gIII fragment and lacZ promoter are spliced by PCR overlap extension (see Horton et al., *Gene*, 77, 61–68 (1989)). The resulting product is digested with Spe I and EcoRI and ligated into the corresponding sites of pcomb to yield pcomb 3'. Finally, pcomb 3' is digested with Xho I and Spe I and ligated with the corresponding 51-base-pair (bp) stuffer from pBluescript (see Short, et al., *Nucleic Acids Res.*, 16, pp. 7583–7600 (1988)) (Stratagene) to yield pComb 3, an ampicillin-resistant phagemid.

Expression of Nucleotides on M13 Phage Coat
Phage Production

A pComb 3 phagemid including a recombinantly produced Fab fragment that immunoreacts with a mercury cation may be transformed into Escherichia coli XL1-Blue cells. The transformed *E. coli* XL1-Blue cells may be grown in-super broth medium (SB; 30 g of tryptone, 20 g of yeast extract, 10 g of Mops per liter, pH 7) at 37° C. supplemented with tetracycline at 10 μg/mi and carbenicillin at 50 μg/ml or chloramphenicol at 30 μg/ml. Cultures are grown to an $OD_{600}$ of 0.4 and infected with VCSM13 helper phage (phage to cell ratio, 20:1) and grown an additional hour. After 1 hr kanamycin is added (70 μg/ml), and the culture is incubated overnight at 30° C. Phage are isolated from liquid culture by polyethylene glycol 8000 and NaCl precipitation as described in Cwirla, et al., *Proc. Natl. Acad. Sci. USA*, 87, pp. 6378–6382 (1990). Phage pellets may be resuspended in phosphate-buffered saline (50 mM phosphate, pH7.2/150 mM NaCl) and stored at −20° C.

Single-Pass Enrichment Experiments. Phage expressing mercuric cation binding Fab fragments on their surface may be enriched by a modification of the panning procedure described by Parmley, et al., *Gene*, 73, pp. 305–318 (1988). A single well of a microtiter plate (Costar 3690) is coated overnight at 4° C. with 25 μl of BSA-glutathione-mercuric ion at 2 mg/ml in 0.1 M bicarbonate, pH 8.5. The well is washed once with water and blocked by filling the well with Blotto (5% (wt/vol) nonfat dry milk in phosphate-buffered saline) and incubating the plate at 37° C. for 1 hr. Blocking solution is shaken out, and 50 μl of clonally mixed phage (typically $10^{11}$ colony-forming units (cfu)) is added, and the plate was incubated for an additional 2 hr at 37° C. Phage are removed, and the well is washed once with distilled water. The well is washed 10 times with TBS/Tween solution (50 mM Tris-HCl, pH 7.5/150 mM NaCl/0.05% Tween 20) over a period of 1 hr at room temperature. The well is washed once more with distilled water, and adherent phage are eluted by adding 50 μl of elution buffer (0.1 M HCl, adjusted to pH 2.2 with glycine, containinq bovine serum albumin) at 1 mg/ml and incubation at room temperature for 10 min. The eluate is removed and neutralized with 3 μl of 2 M Tris base. The initial phage input ratio may be determined by titering on selected plates. The final phage output ratio may be determined by infecting 1 ml of logarithmic phase XL1-Blue cells with the neutralized eluate for 15 min at room temperature and plating equal aliquots on selective carbenicillin and chloramphenicol plates.

EXAMPLE 4

Site Directed Mutagenesis of 4A10 and Expression on Phage Coat

Cloning of 4A10 Fab in pComb3 Vector

RNA from hybridoma 4A10 ATCC deposit No. HB 10381, deposited Mar. 13, 1990 was amplified by PCR as described above with primers that made it possible to amplify the Fd fragment of the heavy chain and the entire kappa chain.

Site Directed Mutagenesis of 4A10 Heavy Chain

Site-directed mutagenesis was carried out via the megaprimer method (see Sarkar et al., *Biotechniques*, 8, 404–407 (1990)) using a primer which replaced the cysteine at position 93 of the heavy chain with a tyrosine or a serine. The mutagenized fragment was electrophoresed, extracted from the agarose gel, and used for amplification of the remainder of the Fd fragment.

This 4A10H cys→tyr(ser) Fd product was cloned in a pComb3 vector which already contained the nucleotide coding for a light chain, e.g., the light chain of 4A10 or the light chain from an antibody, 1C3, which did not immunoreact with a mercury cation (an "irrelevant antibody"). The nucleotide sequence of the mutagenized fragment was determined to confirm the mutations.

Expression of 4A10 Antibody on a Phage Coat

*E. coli* XL-1 Blue was transformed with pComb3 vectors containing the following combinations of antibody genes: p3A3A (heavy and light chains from 4A10), p3A3C (heavy chain from 4A10 and light chain the irrelevant antibody, 1C3), p3C3C (heavy and light chains from 1C3) and $p3A_{cys \rightarrow tyr}3A$ (mutagenized heavy chain and unmodified light chain from 4A10). Bacteria were infected with kanamycin-resistant bacteriophage M13 as described above to produce Phabs displaying one of the above Fab fragments as part of their coat.

Mercuric Ion-ELISA for Phabs

Equal plaque forming units from Phabs obtained from these transformed *E. coli* XL1-Blue cell cultures were incubated at 37° C. for two hours on BSA-Glutathione ELISA plates with or without mercuric nitrate. A rabbit anti-M13 antiserum was used as a second antibody followed by affinity-purified goat-antirabbit serum conjugated with peroxidase. 2,2'-Azino-Di-[3-ethylbenzthiazoline sulfonate] (ABTS) was used as peroxidase substrate. The results, expressed as absorbance at 405 nanometers, are shown in Table VII below.

TABLE VII

Reactivity of Phabs with Glutathione-Mercuric Ions by ELISA

| Phab | Hg-GSH-BSA | GSH-BSA |
|---|---|---|
| p3A3A | 0.917 | 0.244 |
| p3A3C | 1.916 | 0.383 |
| p3C3C | 0.678 | 0.353 |
| $p3A_{CYS \rightarrow TYR}3A$ Clone 1 | 0.150 | 0.232 |
| $p3A_{CYS \rightarrow TYR}3A$ Clone 2 | 0.243 | 0.207 |

The mutation, which introduced a tyrosine in place of cysteine-93 in the cloned Fd heavy chain of the antibody 4A10, produced a decrease in the signal to the same level as background. This result supports the idea cysteine is required for binding to mercury. However, other irrelevant monoclonal antibodies with a cysteine group in the hypervarible region tested negative for reactivity against mercury in ELISA. Hence, it seems that the presence of cysteine is a necessary but not sufficient requisite for binding mercury.

Interestingly, shuffling of the heavy chain of 4A10 with the light chain of the unrelated antibody 1C3 resulted in a better signal in the mercury ion ELISA. This could be due to stabilization of the heavy chain of 4A10 into a conformation more favorable for mercury binding or to an improvement in the affinity for mercury due to greater coordination between the metal and the oxygens in the multiple aspartate residues present in the 1C3 light chain.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

---

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
      (A) LENGTH: 348 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (B) STRAIN: Heavy chain variable region for monoclonal antibody 4A10

(ix) FEATURE:
      (A) NAME/KEY: CDS
      (B) LOCATION: 1..348

(xi) SEQUENCE DESCRIPTION: SEQ ID NO:1:

```
GAG GTT CAG CTG CAG CAG TCT GGA CCT GAG CTG GTG AAG CCT GGG GCT        48
Glu Val Gln Leu Gln Gln Ser Gly Pro Glu Leu Val Lys Pro Gly Ala
  1               5                  10                  15

TTA GTG AAG ATA TCC TGC AAG GCT TCT GGT TAC ACC TTC ACA AGC TAC        96
Leu Val Lys Ile Ser Cys Lys Ala Ser Gly Tyr Thr Phe Thr Ser Tyr
             20                  25                  30

GAT ATA AAC TGG GTG AAG CAG AGG CCT GGA CAG GGA CTT GAG TGG ATT       144
Asp Ile Asn Trp Val Lys Gln Arg Pro Gly Gln Gly Leu Glu Trp Ile
         35                  40                  45

GGA TGG ATT TAT CCT GGA GAT GGT AGT ACT AAG TAC AAT GAG AAA TTC       192
Gly Trp Ile Tyr Pro Gly Asp Gly Ser Thr Lys Tyr Asn Glu Lys Phe
 50                  55                  60

AAG GGC AAG GCC ACA CTG ACT GCA GAC AAA TCC TCC AGC ACA GCC TAC       240
Lys Gly Lys Ala Thr Leu Thr Ala Asp Lys Ser Ser Ser Thr Ala Tyr
 65                  70                  75                  80

ATG CAG CTC AGC AGC CTG ACT TCT GAG AAC TCT GCA GTC TAT TTC TGT       288
Met Gln Leu Ser Ser Leu Thr Ser Glu Asn Ser Ala Val Tyr Phe Cys
                 85                  90                  95

GCA AGA TGC GGC TAT GCT ATG GAC TAC TGG GGT CAA GGA ACC TCA GTC       336
Ala Arg Cys Gly Tyr Ala Met Asp Tyr Trp Gly Gln Gly Thr Ser Val
            100                 105                 110

ACC GTC TCC TCA                                                        348
Thr Val Ser Ser
            115
```

(2) INFORMATION FOR SEQ ID NO:2:

(i) SEQUENCE CHARACTERISTICS:
      (A) LENGTH: 116 amino acids
      (B) TYPE: amino acid
      (D) TOPOLOGY: linear (ii) MOLECULE TYPE: protein (xi) SEQUENCE DESCRIPTION: SEQ ID NO:2:

```
Glu Val Gln Leu Gln Gln Ser Gly Pro Glu Leu Val Lys Pro Gly Ala
 1               5                  10                  15

Leu Val Lys Ile Ser Cys Lys Ala Ser Gly Tyr Thr Phe Thr Ser Tyr
             20                  25                  30

Asp Ile Asn Trp Val Lys Gln Arg Pro Gly Gln Gly Leu Glu Trp Ile
             35                  40                  45

Gly Trp Ile Tyr Pro Gly Asp Gly Ser Thr Lys Tyr Asn Glu Lys Phe
         50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asn Ser Ala Val Tyr Phe Cys
                 85                  90                  95

Ala Arg Cys Gly Tyr Ala Met Asp Tyr Trp Gly Gln Gly Thr Ser Val
             100                 105                 110

Thr Val Ser Ser
         115
```

(2) INFORMATION FOR SEQ ID NO:3:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: Heavy chain variable region for monoclonal
            antibody 1C11

(ix) FEATURE:
        (A) NAME/KEY: CDS
        (B) LOCATION: 1..354

(xi) SEQUENCE DESCRIPTION: SEQ ID NO:3:

```
TCT GGG GCT GAG CTT GTG AAG CCT GGG GCT TCA GTG AAA CTG TCC TGC     48
Ser Gly Ala Glu Leu Val Lys Pro Gly Ala Ser Val Lys Leu Ser Cys
 1               5                  10                  15

AAG ACT TCT GGC TAC ACC GTC ACC AGC TAC TGG ATG GGC TGG GTG AAG     96
Lys Thr Ser Gly Tyr Thr Val Thr Ser Tyr Trp Met Gly Trp Val Lys
             20                  25                  30

CAG AGG CCT GGA CAA GGC CTT GAG TGG ATT GGA AAT ATT TAT CCT GAT    144
Gln Arg Pro Gly Gln Gly Leu Glu Trp Ile Gly Asn Ile Tyr Pro Asp
             35                  40                  45

AGT GGT ACT ACT AAC TAC AAT GAG AAG TTC AAG AAC AAG GCC ACA CTG    192
Ser Gly Thr Thr Asn Tyr Asn Glu Lys Phe Lys Asn Lys Ala Thr Leu
         50                  55                  60

ACT GTA GAC ACA TTC TCC AGC ACA GTC TAC ATG CAG CTC AGC AGC CTG    240
Thr Val Asp Thr Phe Ser Ser Thr Val Tyr Met Gln Leu Ser Ser Leu
 65                  70                  75                  80

ACA TCT GAG GAC TCT GCG GTC TAT TAT TGT GCA AGA GGG GTG TAT AGT    288
Thr Ser Glu Asp Ser Ala Val Tyr Tyr Cys Ala Arg Gly Val Tyr Ser
                 85                  90                  95

TAT TAC AGT TAC GAC GTC TAT GCT ATG GAC TAC TGG GGT CAA GGA ACA    336
Tyr Tyr Ser Tyr Asp Val Tyr Ala Met Asp Tyr Trp Gly Gln Gly Thr
             100                 105                 110

TCA GTC ACC GTC TCC TCA                                             354
Ser Val Thr Val Ser Ser
         115
```

(2) INFORMATION FOR SEQ ID NO:4:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:4:

```
Ser Gly Ala Glu Leu Val Lys Pro Gly Ala Ser Val Lys Leu Ser Cys
 1               5                  10                  15

Lys Thr Ser Gly Tyr Thr Val Thr Ser Tyr Trp Met Gly Trp Val Lys
                20                  25                  30

Gln Arg Pro Gly Gln Gly Leu Glu Trp Ile Gly Asn Ile Tyr Pro Asp
            35                  40                  45

Ser Gly Thr Thr Asn Tyr Asn Glu Lys Phe Lys Asn Lys Ala Thr Leu
        50                  55                  60

Thr Val Asp Thr Phe Ser Ser Thr Val Tyr Met Gln Leu Ser Ser Leu
65                  70                  75                  80

Thr Ser Glu Asp Ser Ala Val Tyr Tyr Cys Ala Arg Gly Val Tyr Ser
                85                  90                  95

Tyr Tyr Ser Tyr Asp Val Tyr Ala Met Asp Tyr Trp Gly Gln Gly Thr
            100                 105                 110

Ser Val Thr Val Ser Ser
        115
```

(2) INFORMATION FOR SEQ ID NO:5:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: Heavy chain variable region for monoclonal
            antibody 5G4

(ix) FEATURE:
        (A) NAME/KEY: CDS
        (B) LOCATION: 1..324

(xi) SEQUENCE DESCRIPTION: SEQ ID NO:5:

```
TCT GTA CCG GCG CGN TTG AAG CCT GGG GCT TCA GTG AGG ATA TCC TGC      48
Ser Val Pro Ala Arg Leu Lys Pro Gly Ala Ser Val Arg Ile Ser Cys
 1               5                  10                  15

AAG GCT TCT GCT TAC TCA TTT ACT GGC TAC TTT ATG AAC TGG ATG AAG      96
Lys Ala Ser Ala Tyr Ser Phe Thr Gly Tyr Phe Met Asn Trp Met Lys
                20                  25                  30

CAG AGC CAT GGA AAG ACC CTT GAG TGG ATT GGA CGT ATT AAT CCT TAC     144
Gln Ser His Gly Lys Thr Leu Glu Trp Ile Gly Arg Ile Asn Pro Tyr
            35                  40                  45

AAT GGT GAT ACT TTC TAT AAC CAG AAG TTC AAG AGC AAG GCC ACA GTA     192
Asn Gly Asp Thr Phe Tyr Asn Gln Lys Phe Lys Ser Lys Ala Thr Val
        50                  55                  60

ACT GTA GAC AAA TCC TCT AGC ACA GCC CAC ATG GAG CTC CTG AGC CTG     240
Thr Val Asp Lys Ser Ser Ser Thr Ala His Met Glu Leu Leu Ser Leu
65                  70                  75                  80

ACA TCT GAG GAC TCT GCA GTC TAT TAT TGT GGA ACC CAG CCC CTT GAC     288
Thr Ser Glu Asp Ser Ala Val Tyr Tyr Cys Gly Thr Gln Pro Leu Asp
                85                  90                  95
```

```
TAC TGG GGC CAA GGC ACC ACT CTC ACA GTC TCC TCA                          324
Tyr Trp Gly Gln Gly Thr Thr Leu Thr Val Ser Ser
            100                 105
```

(2) INFORMATION FOR SEQ ID NO:6:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO:6:

```
Ser Val Pro Ala Arg Leu Lys Pro Gly Ala Ser Val Arg Ile Ser Cys
 1               5                  10                  15

Lys Ala Ser Ala Tyr Ser Phe Thr Gly Tyr Phe Met Asn Trp Met Lys
                20                  25                  30

Gln Ser His Gly Lys Thr Leu Glu Trp Ile Gly Arg Ile Asn Pro Tyr
            35                  40                  45

Asn Gly Asp Thr Phe Tyr Asn Gln Lys Phe Lys Ser Lys Ala Thr Val
        50                  55                  60

Thr Val Asp Lys Ser Ser Ser Thr Ala His Met Glu Leu Leu Ser Leu
65                  70                  75                  80

Thr Ser Glu Asp Ser Ala Val Tyr Tyr Cys Gly Thr Gln Pro Leu Asp
                85                  90                  95

Tyr Trp Gly Gln Gly Thr Thr Leu Thr Val Ser Ser
            100                 105
```

(2) INFORMATION FOR SEQ ID NO:7:

(i) SEQUENCE CHARACTERISTICS:
        (A) LENGTH: 344 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: Heavy chain variable region for monoclonal
            antibody 23F8

(ix) FEATURE:
        (A) NAME/KEY: CDS
        (B) LOCATION: 1..344

(xi) SEQUENCE DESCRIPTION: SEQ ID NO:7:

```
TCT GGA CCT GAG CTA GTG AAG ACT GGG GCT TCA GTG AAG ATA TCC TGC          48
Ser Gly Pro Glu Leu Val Lys Thr Gly Ala Ser Val Lys Ile Ser Cys
 1               5                  10                  15

AAG GCT TCT GGT TAC TCA TTC ACT GGT TAC TAC ATG CAC TGG GTC AAG          96
Lys Ala Ser Gly Tyr Ser Phe Thr Gly Tyr Tyr Met His Trp Val Lys
                20                  25                  30

CAG AGC CAT GGA AAG AGC CTT GAG TGG ATT GGA TAT ATT AGT TGT TAC         144
Gln Ser His Gly Lys Ser Leu Glu Trp Ile Gly Tyr Ile Ser Cys Tyr
            35                  40                  45

AAT GGT GCT ACT AGC TAC AAC CAG AAG TTC AAG GGC AAG GCC ACA TTT         192
Asn Gly Ala Thr Ser Tyr Asn Gln Lys Phe Lys Gly Lys Ala Thr Phe
        50                  55                  60

ACT GTA GAC ACA TCC TCC AGC ACA GCC TAC ATG CAG TTC AAC AGC CTG         240
Thr Val Asp Thr Ser Ser Ser Thr Ala Tyr Met Gln Phe Asn Ser Leu
65                  70                  75                  80

ACA TCT GAA GAC TCT GCN GTC TAT TAC TGT GCA AGA TCC GGG ATC TAT         288
```

```
Thr Ser Glu Asp Ser Ala Val Tyr Tyr Cys Ala Arg Ser Gly Ile Tyr
            85                  90                  95

GAT GTT ACT ACT ACT TTG ACT ACT GGG GCC AAG GCA CCA CTC TCA CAG       336
Asp Val Thr Thr Thr Leu Thr Thr Gly Ala Lys Ala Pro Leu Ser Gln
        100                 105                 110

TCT CCT CA                                                            344
Ser Pro
```

(2) INFORMATION FOR SEQ ID NO:8:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO:8:

```
Ser Gly Pro Glu Leu Val Lys Thr Gly Ala Ser Val Lys Ile Ser Cys
 1               5                  10                  15

Lys Ala Ser Gly Tyr Ser Phe Thr Gly Tyr Tyr Met His Trp Val Lys
                20                  25                  30

Gln Ser His Gly Lys Ser Leu Glu Trp Ile Gly Tyr Ile Ser Cys Tyr
            35                  40                  45

Asn Gly Ala Thr Ser Tyr Asn Gln Lys Phe Lys Gly Lys Ala Thr Phe
 50                  55                  60

Thr Val Asp Thr Ser Ser Ser Thr Ala Tyr Met Gln Phe Asn Ser Leu
 65                  70                  75                  80

Thr Ser Glu Asp Ser Ala Val Tyr Tyr Cys Ala Arg Ser Gly Ile Tyr
            85                  90                  95

Asp Val Thr Thr Thr Leu Thr Thr Gly Ala Lys Ala Pro Leu Ser Gln
        100                 105                 110

Ser Pro
```

(2) INFORMATION FOR SEQ ID NO:9:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: Heavy chain variable region for monoclonal
            antibody 2D5

(ix) FEATURE:
        (A) NAME/KEY: CDS
        (B) LOCATION: 1..348

(xi) SEQUENCE DESCRIPTION: SEQ ID NO:9:

```
TCT GGA GGA GGC TCA GTG AAG CCT GGA GGG TCC CTG AAA CTC TCC TGT        48
Ser Gly Gly Gly Ser Val Lys Pro Gly Gly Ser Leu Lys Leu Ser Cys
 1               5                  10                  15

GCA GCC TCT GGA TTC ACT TTC AGT AGC TGT GCC ATG TCT TGG GTT CGC        96
Ala Ala Ser Gly Phe Thr Phe Ser Ser Cys Ala Met Ser Trp Val Arg
                20                  25                  30

CAG ACT CCG GAG AAG AGG CTG GAG TGG GTC GCA ACC ATT AGC AGT GGT       144
Gln Thr Pro Glu Lys Arg Leu Glu Trp Val Ala Thr Ile Ser Ser Gly
            35                  40                  45

GGT AGT TAC ACC TAC TAT CCA GAC AGT GTG AAG GGT CGA TTC ACC ATC       192
Gly Ser Tyr Thr Tyr Tyr Pro Asp Ser Val Lys Gly Arg Phe Thr Ile
```

```
                 50                        55                         60
TTC AGA CAC AAT GCC GAA AAC ACC CTG TAC CTT CAA ATG AGC AGT CTG             240
Phe Arg His Asn Ala Glu Asn Thr Leu Tyr Leu Gln Met Ser Ser Leu
 65                         70                         75                  80

AGG TCT GAG GAC ACG GCC ATA TAT TAT TGT GTT AGA CAG GAC GGC TAC             288
Arg Ser Glu Asp Thr Ala Ile Tyr Tyr Cys Val Arg Gln Asp Gly Tyr
                            85                         90                  95

TAT GGC AAC TAC GTA TGG TTT GCT TAC TGG GGC CAA GGG ACT CTG GTC             336
Tyr Gly Asn Tyr Val Trp Phe Ala Tyr Trp Gly Gln Gly Thr Leu Val
                    100                        105                        110

ACT GTC TCT GCA                                                             348
Thr Val Ser Ala
        115

(2) INFORMATION FOR SEQ ID NO:10:

(i) SEQUENCE CHARACTERISTICS:
         (A) LENGTH: 116 amino acids
         (B) TYPE: amino acid
         (D) TOPOLOGY: linear (ii) MOLECULE TYPE: protein (xi) SEQUENCE DESCRIPTION: SEQ ID NO:10:

Ser Gly Gly Gly Ser Val Lys Pro Gly Gly Ser Leu Lys Leu Ser Cys
 1               5                  10                  15

Ala Ala Ser Gly Phe Thr Phe Ser Ser Cys Ala Met Ser Trp Val Arg
                20                  25                  30

Gln Thr Pro Glu Lys Arg Leu Glu Trp Val Ala Thr Ile Ser Ser Gly
            35                  40                  45

Gly Ser Tyr Thr Tyr Tyr Pro Asp Ser Val Lys Gly Arg Phe Thr Ile
        50                  55                  60

Phe Arg His Asn Ala Glu Asn Thr Leu Tyr Leu Gln Met Ser Ser Leu
 65                 70                  75                  80

Arg Ser Glu Asp Thr Ala Ile Tyr Tyr Cys Val Arg Gln Asp Gly Tyr
                85                  90                  95

Tyr Gly Asn Tyr Val Trp Phe Ala Tyr Trp Gly Gln Gly Thr Leu Val
               100                 105                 110

Thr Val Ser Ala
       115

(2) INFORMATION FOR SEQ ID NO:11:

(i) SEQUENCE CHARACTERISTICS:
         (A) LENGTH: 348 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (B) STRAIN: Heavy chain variable region for monoclonal
             antibody 5B6

(ix) FEATURE:
         (A) NAME/KEY: CDS
         (B) LOCATION: 1..348

(xi) SEQUENCE DESCRIPTION: SEQ ID NO:11:

TCT GGA GGA GGC TCA GTG AAG CCT GGA GGG TCC CTG AAG CTC TCC TGT              48
Ser Gly Gly Gly Ser Val Lys Pro Gly Gly Ser Leu Lys Leu Ser Cys
 1               5                  10                  15

GCA GCC TCT GGA TTC ACT TTC AGT AGC CGT GCC ATG TCT TGG GTT CGC              96
```

|  |  |  |  |  |  |  |  |  |  |  |  |  |
|---|---|---|---|---|---|---|---|---|---|---|---|---|
| Ala | Ala | Ser | Gly | Phe | Thr | Phe | Ser | Ser | Arg | Ala | Met | Ser | Trp | Val | Arg |
|  |  |  | 20 |  |  |  |  | 25 |  |  |  |  | 30 |  |  |

```
CAG ACT CCG GAG AAG AGG CTG GAG TGG GTC GCA ACC ATT AGC AGT GGT      144
Gln Thr Pro Glu Lys Arg Leu Glu Trp Val Ala Thr Ile Ser Ser Gly
         35                  40                  45

GGT AGT TAC ACC TAC TAT CCA GAC AGT GTG AAG GGT CGA TTC ACC ATC      192
Gly Ser Tyr Thr Tyr Tyr Pro Asp Ser Val Lys Gly Arg Phe Thr Ile
 50                  55                  60

TCC AGA CAC AAT GCC GAA AAC ACC CTG TAC TTT CAA ATG AGC AGT CTG      240
Ser Arg His Asn Ala Glu Asn Thr Leu Tyr Phe Gln Met Ser Ser Leu
 65                  70                  75                  80

AGG TCT GAG GAC ACG GCA ATA TAT TAT TGT GTT AGA CAG ACG GGT TAC      288
Arg Ser Glu Asp Thr Ala Ile Tyr Tyr Cys Val Arg Gln Thr Gly Tyr
                 85                  90                  95

TAT GGC AAC TAC GAA TGG TTT GCT TAC TGG GGC CAA GGA CTT CTG GTA      336
Tyr Gly Asn Tyr Glu Trp Phe Ala Tyr Trp Gly Gln Gly Leu Leu Val
                100                 105                 110

ACT GTT TCT GCA                                                      348
Thr Val Ser Ala
        115
```

(2) INFORMATION FOR SEQ ID NO:12:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:12:

```
Ser Gly Gly Gly Ser Val Lys Pro Gly Gly Ser Leu Lys Leu Ser Cys
 1               5                  10                  15

Ala Ala Ser Gly Phe Thr Phe Ser Ser Arg Ala Met Ser Trp Val Arg
             20                  25                  30

Gln Thr Pro Glu Lys Arg Leu Glu Trp Val Ala Thr Ile Ser Ser Gly
         35                  40                  45

Gly Ser Tyr Thr Tyr Tyr Pro Asp Ser Val Lys Gly Arg Phe Thr Ile
 50                  55                  60

Ser Arg His Asn Ala Glu Asn Thr Leu Tyr Phe Gln Met Ser Ser Leu
 65                  70                  75                  80

Arg Ser Glu Asp Thr Ala Ile Tyr Tyr Cys Val Arg Gln Thr Gly Tyr
                 85                  90                  95

Tyr Gly Asn Tyr Glu Trp Phe Ala Tyr Trp Gly Gln Gly Leu Leu Val
                100                 105                 110

Thr Val Ser Ala
        115
```

(2) INFORMATION FOR SEQ ID NO:13:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: Light chain variable region for monoclonal
            antibody 1F10

(ix) FEATURE:
        (A) NAME/KEY: CDS (B) LOCATION: 1..321

(xi) SEQUENCE DESCRIPTION: SEQ ID NO:13:

```
GAC ATC CAG ATG ACC CAG TCT CCA TCC TCC TTA TCT GCC TCT CTG GGA      48
Asp Ile Gln Met Thr Gln Ser Pro Ser Ser Leu Ser Ala Ser Leu Gly
 1               5                  10                  15

GAA AGA GTC ACT CTC ACT TGT CGG GCC AGT CAG GAC ATT GGT AGT AGT      96
Glu Arg Val Thr Leu Thr Cys Arg Ala Ser Gln Asp Ile Gly Ser Ser
                20                  25                  30

TTA AAC TGG CTT CAG CTG AAA CCA GAT GGA ACT ATT AAA CGC CTG ATC     144
Leu Asn Trp Leu Gln Leu Lys Pro Asp Gly Thr Ile Lys Arg Leu Ile
            35                  40                  45

TAC GCC ACA TCC GGT TTA GAT TCT GGT GTC CCC AAA AGG TTC AGT GGC     192
Tyr Ala Thr Ser Gly Leu Asp Ser Gly Val Pro Lys Arg Phe Ser Gly
        50                  55                  60

AGT AGG TCT GGG TCA GAT TAT TCT CTC ACC ATC AAC AGC CCT GAG TCT     240
Ser Arg Ser Gly Ser Asp Tyr Ser Leu Thr Ile Asn Ser Pro Glu Ser
 65                  70                  75                  80

GAA GAT TTT GTA GAC TAT TAC TGT CTA CAA TGT TCT AAT TCT CCG TAC     288
Glu Asp Phe Val Asp Tyr Tyr Cys Leu Gln Cys Ser Asn Ser Pro Tyr
                85                  90                  95

ACG TTC GGA GGG GGG ACC AAG CTG GAA ATA AAA                         321
Thr Phe Gly Gly Gly Thr Lys Leu Glu Ile Lys
                100                 105
```

(2) INFORMATION FOR SEQ ID NO:14:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:14:

```
Asp Ile Gln Met Thr Gln Ser Pro Ser Ser Leu Ser Ala Ser Leu Gly
 1               5                  10                  15

Glu Arg Val Thr Leu Thr Cys Arg Ala Ser Gln Asp Ile Gly Ser Ser
                20                  25                  30

Leu Asn Trp Leu Gln Leu Lys Pro Asp Gly Thr Ile Lys Arg Leu Ile
            35                  40                  45

Tyr Ala Thr Ser Gly Leu Asp Ser Gly Val Pro Lys Arg Phe Ser Gly
        50                  55                  60

Ser Arg Ser Gly Ser Asp Tyr Ser Leu Thr Ile Asn Ser Pro Glu Ser
 65                  70                  75                  80

Glu Asp Phe Val Asp Tyr Tyr Cys Leu Gln Cys Ser Asn Ser Pro Tyr
                85                  90                  95

Thr Phe Gly Gly Gly Thr Lys Leu Glu Ile Lys
                100                 105
```

(2) INFORMATION FOR SEQ ID NO:15:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: Light chain variable region for monoclonal
            antibody 4A10

(ix) FEATURE:
    (A) NAME/KEY: CDS
    (B) LOCATION: 1..336

(xi) SEQUENCE DESCRIPTION: SEQ ID NO:15:

| | | | | | | | | | | | | | | | | |
|---|---|---|---|---|---|---|---|---|---|---|---|---|---|---|---|---|
| GAT | GTT | TTG | ATG | ACC | CAA | ACT | CCA | CTC | TCC | CTG | CCT | GTC | AGT | CTT | GGA | 48 |
| Asp | Val | Leu | Met | Thr | Gln | Thr | Pro | Leu | Ser | Leu | Pro | Val | Ser | Leu | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GAT | CAA | GCC | TCC | ATC | TCT | TGC | AGA | TCT | AGT | CAG | AGC | ATT | GTA | CAT | AGT | 96 |
| Asp | Gln | Ala | Ser | Ile | Ser | Cys | Arg | Ser | Ser | Gln | Ser | Ile | Val | His | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| AAT | GGA | AAC | ACC | TAT | TTA | GAA | TGG | TAC | CTG | CAG | AAA | CCA | GGC | CAG | TCT | 144 |
| Asn | Gly | Asn | Thr | Tyr | Leu | Glu | Trp | Tyr | Leu | Gln | Lys | Pro | Gly | Gln | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| CCA | AAG | CTC | CTG | ATC | TAC | AAA | GTT | TCC | AAC | CGA | TTT | TCT | GGG | GTC | CCA | 192 |
| Pro | Lys | Leu | Leu | Ile | Tyr | Lys | Val | Ser | Asn | Arg | Phe | Ser | Gly | Val | Pro | |
| 50 | | | | | 55 | | | | | 60 | | | | | | |

| | | | | | | | | | | | | | | | | |
|---|---|---|---|---|---|---|---|---|---|---|---|---|---|---|---|---|
| GAC | AGG | TTC | AGT | GGC | AGT | GGA | TCA | GGG | ACA | GAT | TTC | ACA | CTC | AAG | ATC | 240 |
| Asp | Arg | Phe | Ser | Gly | Ser | Gly | Ser | Gly | Thr | Asp | Phe | Thr | Leu | Lys | Ile | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| AGC | AGA | GCG | GAG | GCT | GAG | GAT | CTG | GGA | GTT | TAT | TAC | TGC | TTT | CAA | GGT | 288 |
| Ser | Arg | Ala | Glu | Ala | Glu | Asp | Leu | Gly | Val | Tyr | Tyr | Cys | Phe | Gln | Gly | |
| | | | 85 | | | | | 90 | | | | | 95 | | | |

| | | | | | | | | | | | | | | | | |
|---|---|---|---|---|---|---|---|---|---|---|---|---|---|---|---|---|
| TCA | CAT | GTT | CGG | TAC | ACG | TTC | GGT | GGA | GGC | ACC | AAG | CTG | GAA | ATC | AAA | 336 |
| Ser | His | Val | Arg | Tyr | Thr | Phe | Gly | Gly | Gly | Thr | Lys | Leu | Glu | Ile | Lys | |
| | | | 100 | | | | | 105 | | | | | 110 | | | |

(2) INFORMATION FOR SEQ ID NO:16:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:16:

| | | | | | | | | | | | | | | |
|---|---|---|---|---|---|---|---|---|---|---|---|---|---|---|
| Asp | Val | Leu | Met | Thr | Gln | Thr | Pro | Leu | Ser | Leu | Pro | Val | Ser | Leu | Gly |
| 1 | | | | 5 | | | | | 10 | | | | | 15 | |

| | | | | | | | | | | | | | | | |
|---|---|---|---|---|---|---|---|---|---|---|---|---|---|---|---|
| Asp | Gln | Ala | Ser | Ile | Ser | Cys | Arg | Ser | Ser | Gln | Ser | Ile | Val | His | Ser |
| | | | 20 | | | | | 25 | | | | | 30 | | |

| | | | | | | | | | | | | | | | |
|---|---|---|---|---|---|---|---|---|---|---|---|---|---|---|---|
| Asn | Gly | Asn | Thr | Tyr | Leu | Glu | Trp | Tyr | Leu | Gln | Lys | Pro | Gly | Gln | Ser |
| | | 35 | | | | | 40 | | | | | 45 | | | |

| | | | | | | | | | | | | | | | |
|---|---|---|---|---|---|---|---|---|---|---|---|---|---|---|---|
| Pro | Lys | Leu | Leu | Ile | Tyr | Lys | Val | Ser | Asn | Arg | Phe | Ser | Gly | Val | Pro |
| 50 | | | | | 55 | | | | | 60 | | | | | |

| | | | | | | | | | | | | | | | |
|---|---|---|---|---|---|---|---|---|---|---|---|---|---|---|---|
| Asp | Arg | Phe | Ser | Gly | Ser | Gly | Ser | Gly | Thr | Asp | Phe | Thr | Leu | Lys | Ile |
| 65 | | | | 70 | | | | | 75 | | | | | 80 | |

| | | | | | | | | | | | | | | | |
|---|---|---|---|---|---|---|---|---|---|---|---|---|---|---|---|
| Ser | Arg | Ala | Glu | Ala | Glu | Asp | Leu | Gly | Val | Tyr | Tyr | Cys | Phe | Gln | Gly |
| | | | 85 | | | | | 90 | | | | | 95 | | |

| | | | | | | | | | | | | | | | |
|---|---|---|---|---|---|---|---|---|---|---|---|---|---|---|---|
| Ser | His | Val | Arg | Tyr | Thr | Phe | Gly | Gly | Gly | Thr | Lys | Leu | Glu | Ile | Lys |
| | | | 100 | | | | | 105 | | | | | 110 | | |

(2) INFORMATION FOR SEQ ID NO:17:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: Light chain variable region for monoclonal antibody 1C11

(ix) FEATURE:
    (A) NAME/KEY: CDS
    (B) LOCATION: 1..336

(xi) SEQUENCE DESCRIPTION: SEQ ID NO:17:

```
GAC TTA GTG CTT ACA CAG TCT CCT CCT TCC TTA GCT GTA TCT CTG GGG        48
Asp Leu Val Leu Thr Gln Ser Pro Pro Ser Leu Ala Val Ser Leu Gly
 1               5                  10                  15

CAG AGG TCC ACC ATC TCT TGC AGA TCT AGT CAG AGC ATT GTA CAT AGT        96
Gln Arg Ser Thr Ile Ser Cys Arg Ser Ser Gln Ser Ile Val His Ser
                20                  25                  30

AAT GGA AAC ACC TAT TTG CAC TGG TAC CAA CAG AAT CCA GGG CAG CCA       144
Asn Gly Asn Thr Tyr Leu His Trp Tyr Gln Gln Asn Pro Gly Gln Pro
            35                  40                  45

CCG AAA CTC CTC ATC AAG TAT GCA TCC AAC CTA GAA TCT GGG GTC CCT       192
Pro Lys Leu Leu Ile Lys Tyr Ala Ser Asn Leu Glu Ser Gly Val Pro
    50                  55                  60

GCC AGG TTC AGT GGC AGT GGG TCT GGG ACA GAC TTC ACC CTC AAC ATC       240
Ala Arg Phe Ser Gly Ser Gly Ser Gly Thr Asp Phe Thr Leu Asn Ile
65                  70                  75                  80

CAT CCT GCG GAG GTG GAA GAT AGT GCA ACA TAT TTC TGT CAA CAC AGT       288
His Pro Ala Glu Val Glu Asp Ser Ala Thr Tyr Phe Cys Gln His Ser
                85                  90                  95

TGG GAG ATT CCT CCG ACG TTC GGT GGA GGC ACC AAG TTG GAA ATC AAA       336
Trp Glu Ile Pro Pro Thr Phe Gly Gly Gly Thr Lys Leu Glu Ile Lys
                100                 105                 110
```

(2) INFORMATION FOR SEQ ID NO:18:

(i) SEQUENCE CHARACTERISTICS:
       (A) LENGTH: 112 amino acids
       (B) TYPE: amino acid
       (D) TOPOLOGY: linear (ii) MOLECULE TYPE: protein (xi) SEQUENCE DESCRIPTION: SEQ ID NO:18:

```
Asp Leu Val Leu Thr Gln Ser Pro Pro Ser Leu Ala Val Ser Leu Gly
 1               5                  10                  15

Gln Arg Ser Thr Ile Ser Cys Arg Ser Ser Gln Ser Ile Val His Ser
                20                  25                  30

Asn Gly Asn Thr Tyr Leu His Trp Tyr Gln Gln Asn Pro Gly Gln Pro
            35                  40                  45

Pro Lys Leu Leu Ile Lys Tyr Ala Ser Asn Leu Glu Ser Gly Val Pro
    50                  55                  60

Ala Arg Phe Ser Gly Ser Gly Ser Gly Thr Asp Phe Thr Leu Asn Ile
65                  70                  75                  80

His Pro Ala Glu Val Glu Asp Ser Ala Thr Tyr Phe Cys Gln His Ser
                85                  90                  95

Trp Glu Ile Pro Pro Thr Phe Gly Gly Gly Thr Lys Leu Glu Ile Lys
                100                 105                 110
```

(2) INFORMATION FOR SEQ ID NO:19:

(i) SEQUENCE CHARACTERISTICS:
       (A) LENGTH: 321 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
    (B) STRAIN: Light chain variable region for monoclonal
        antibody 5G4

(ix) FEATURE:
    (A) NAME/KEY: CDS
    (B) LOCATION: 1..321

(xi) SEQUENCE DESCRIPTION: SEQ ID NO:19:

| | | | | | | | | | | | | | | | | |
|---|---|---|---|---|---|---|---|---|---|---|---|---|---|---|---|---|
| GAC | ATC | CAG | ATG | ACC | CAG | TCT | CCA | TCC | TCC | TTA | TCT | GCC | TCT | CTG | GGA | 48 |
| Asp | Ile | Gln | Met | Thr | Gln | Ser | Pro | Ser | Ser | Leu | Ser | Ala | Ser | Leu | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GAA | AGA | GTC | ACT | CTC | ACT | TGT | CGG | GCC | AGT | CAG | GAC | ATT | GGT | AGT | AGT | 96 |
| Glu | Arg | Val | Thr | Leu | Thr | Cys | Arg | Ala | Ser | Gln | Asp | Ile | Gly | Ser | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| TTA | AAC | TGG | CTT | CAG | CTG | AAA | CCA | GAT | GGA | ACT | ATT | AAA | CGC | CTG | ATC | 144 |
| Leu | Asn | Trp | Leu | Gln | Leu | Lys | Pro | Asp | Gly | Thr | Ile | Lys | Arg | Leu | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| TAC | GCC | ACA | TCC | GGT | TTA | GAT | TCT | GGT | GTC | CCC | AAA | AGG | TTC | AGT | GGC | 192 |
| Tyr | Ala | Thr | Ser | Gly | Leu | Asp | Ser | Gly | Val | Pro | Lys | Arg | Phe | Ser | Gly | |
| 50 | | | | | 55 | | | | | 60 | | | | | | |

| | | | | | | | | | | | | | | | | |
|---|---|---|---|---|---|---|---|---|---|---|---|---|---|---|---|---|
| AGT | AGG | TCT | GGG | TCA | GAT | TAT | TCT | CTC | ACC | ATC | AAC | AGC | CCT | GAG | TCT | 240 |
| Ser | Arg | Ser | Gly | Ser | Asp | Tyr | Ser | Leu | Thr | Ile | Asn | Ser | Pro | Glu | Ser | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| GAA | GAT | TTT | GTA | GAC | TAT | TAC | TGT | CTA | CAA | TGT | TCT | AAT | TCT | CCG | TAC | 288 |
| Glu | Asp | Phe | Val | Asp | Tyr | Tyr | Cys | Leu | Gln | Cys | Ser | Asn | Ser | Pro | Tyr | |
| | | | 85 | | | | | 90 | | | | | 95 | | | |

| | | | | | | | | | |
|---|---|---|---|---|---|---|---|---|---|
| ACG | TTC | GGA | GGG | GGG | ACC | AAG | CTG | GAA | ATA | AAA | 321 |
| Thr | Phe | Gly | Gly | Gly | Thr | Lys | Leu | Glu | Ile | Lys | |
| | | | 100 | | | | | 105 | | | |

(2) INFORMATION FOR SEQ ID NO:20:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:20:

Asp Ile Gln Met Thr Gln Ser Pro Ser Ser Leu Ser Ala Ser Leu Gly
1               5                   10                  15

Glu Arg Val Thr Leu Thr Cys Arg Ala Ser Gln Asp Ile Gly Ser Ser
            20                  25                  30

Leu Asn Trp Leu Gln Leu Lys Pro Asp Gly Thr Ile Lys Arg Leu Ile
        35                  40                  45

Tyr Ala Thr Ser Gly Leu Asp Ser Gly Val Pro Lys Arg Phe Ser Gly
50                  55                  60

Ser Arg Ser Gly Ser Asp Tyr Ser Leu Thr Ile Asn Ser Pro Glu Ser
65              70                  75                  80

Glu Asp Phe Val Asp Tyr Tyr Cys Leu Gln Cys Ser Asn Ser Pro Tyr
                85                  90                  95

Thr Phe Gly Gly Gly Thr Lys Leu Glu Ile Lys
            100                 105

(2) INFORMATION FOR SEQ ID NO:21:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
     (B) STRAIN: Light chain variable region for monoclonal
         antibody 23F8

(ix) FEATURE:
     (A) NAME/KEY: CDS
     (B) LOCATION: 1..321

(xi) SEQUENCE DESCRIPTION: SEQ ID NO:21:

```
GAC ATC CAG ATG ACC CAG TCT CCA TCC TCA CTG TCT GCA TCT CTG GGA    48
Asp Ile Gln Met Thr Gln Ser Pro Ser Ser Leu Ser Ala Ser Leu Gly
 1               5                  10                  15

GGC AAA GTC ACC ATC ACT TGC AAG GCA AGC CAA GAC ATT AAC AAG TAT    96
Gly Lys Val Thr Ile Thr Cys Lys Ala Ser Gln Asp Ile Asn Lys Tyr
                 20                  25                  30

ATA GCT TGG TAC CAA CAC AAG CCT GGA AAA GGT CCT AGG CTG CTC ATA   144
Ile Ala Trp Tyr Gln His Lys Pro Gly Lys Gly Pro Arg Leu Leu Ile
             35                  40                  45

CAT TAC ACA TCT ACA TTA CAG CCA GGC ATC CCA TCA AGG TTC AGT GGA   192
His Tyr Thr Ser Thr Leu Gln Pro Gly Ile Pro Ser Arg Phe Ser Gly
 50                  55                  60

AGT GGG TCT GGG AGA GAT TAT TCC TTC AGC ATC AGC AAC CCG GAG CCT   240
Ser Gly Ser Gly Arg Asp Tyr Ser Phe Ser Ile Ser Asn Pro Glu Pro
 65                  70                  75                  80

GAA GAT ATT GCA ACT TAT TAT TGT CTA CAG TAT GAT AAT TCT CTG TTC   288
Glu Asp Ile Ala Thr Tyr Tyr Cys Leu Gln Tyr Asp Asn Ser Leu Phe
                 85                  90                  95

ACG TTC GGC TCG GGG ACA AAG TTG GAA ATA AAA                       321
Thr Phe Gly Ser Gly Thr Lys Leu Glu Ile Lys
                100                 105
```

(2) INFORMATION FOR SEQ ID NO:22:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:22:

```
Asp Ile Gln Met Thr Gln Ser Pro Ser Ser Leu Ser Ala Ser Leu Gly
 1               5                  10                  15

Gly Lys Val Thr Ile Thr Cys Lys Ala Ser Gln Asp Ile Asn Lys Tyr
                 20                  25                  30

Ile Ala Trp Tyr Gln His Lys Pro Gly Lys Gly Pro Arg Leu Leu Ile
             35                  40                  45

His Tyr Thr Ser Thr Leu Gln Pro Gly Ile Pro Ser Arg Phe Ser Gly
 50                  55                  60

Ser Gly Ser Gly Arg Asp Tyr Ser Phe Ser Ile Ser Asn Pro Glu Pro
 65                  70                  75                  80

Glu Asp Ile Ala Thr Tyr Tyr Cys Leu Gln Tyr Asp Asn Ser Leu Phe
                 85                  90                  95

Thr Phe Gly Ser Gly Thr Lys Leu Glu Ile Lys
                100                 105
```

(2) INFORMATION FOR SEQ ID NO:23:

(i) SEQUENCE CHARACTERISTICS:
        (A) LENGTH: 321 base pairs
        (B) TYPE: nucleic acid
        (C) STRANDEDNESS: single (D) TOPOLOGY: linear (ii) MOLECULE TYPE: DNA (genomic)

(vi) ORIGINAL SOURCE:
    (B) STRAIN: Light chain variable region for monoclonal
        antibody 2D5

(ix) FEATURE:
    (A) NAME/KEY: CDS
    (B) LOCATION: 1..321

(xi) SEQUENCE DESCRIPTION: SEQ ID NO:23:

```
GAG CTC GTG ATG ACC CAG TCT CCA GCC TCC CTA TCT GCA TCT GTG GGA        48
Glu Leu Val Met Thr Gln Ser Pro Ala Ser Leu Ser Ala Ser Val Gly
 1               5                  10                  15

GAA ACT GTC ACC ATC ACA TGT CGA GCA AGT GAG AAT ATT TAC GGT TAT        96
Glu Thr Val Thr Ile Thr Cys Arg Ala Ser Glu Asn Ile Tyr Gly Tyr
                20                  25                  30

TTA GCA TGG TAT CAG CAG AAA CAG GGA AAA TCT CCT CTG CCC CGG GTC       144
Leu Ala Trp Tyr Gln Gln Lys Gln Gly Lys Ser Pro Leu Pro Arg Val
         35                  40                  45

TAT AAT GCA AAA ACC TTA GCA GAG GAT GTG TCA TCA AGG GTC AGT GGC       192
Tyr Asn Ala Lys Thr Leu Ala Glu Asp Val Ser Ser Arg Val Ser Gly
     50                  55                  60

AGT GGA TCA GGC ACA CAG TTT TCT CTG AAG ATC AGG ACA TCG CAG CCT       240
Ser Gly Ser Gly Thr Gln Phe Ser Leu Lys Ile Arg Thr Ser Gln Pro
 65                  70                  75                  80

GAA GAT TTT GGG ACT TAT TAC TGT CAA CAT CAT TAT GGT ACT CCG TAC       288
Glu Asp Phe Gly Thr Tyr Tyr Cys Gln His His Tyr Gly Thr Pro Tyr
                 85                  90                  95

ACG TTC GGA GGG GGG ACC AAG CTG GAA ATA AAA                           321
Thr Phe Gly Gly Gly Thr Lys Leu Glu Ile Lys
                100                 105
```

(2) INFORMATION FOR SEQ ID NO:24:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:24:

```
Glu Leu Val Met Thr Gln Ser Pro Ala Ser Leu Ser Ala Ser Val Gly
 1               5                  10                  15

Glu Thr Val Thr Ile Thr Cys Arg Ala Ser Glu Asn Ile Tyr Gly Tyr
                20                  25                  30

Leu Ala Trp Tyr Gln Gln Lys Gln Gly Lys Ser Pro Leu Pro Arg Val
         35                  40                  45

Tyr Asn Ala Lys Thr Leu Ala Glu Asp Val Ser Ser Arg Val Ser Gly
     50                  55                  60

Ser Gly Ser Gly Thr Gln Phe Ser Leu Lys Ile Arg Thr Ser Gln Pro
 65                  70                  75                  80

Glu Asp Phe Gly Thr Tyr Tyr Cys Gln His His Tyr Gly Thr Pro Tyr
                 85                  90                  95

Thr Phe Gly Gly Gly Thr Lys Leu Glu Ile Lys
                100                 105
```

(2) INFORMATION FOR SEQ ID NO:25:

(i) SEQUENCE CHARACTERISTICS:
        (A) LENGTH: 321 base pairs (B) TYPE: nucleic acid
(C) STRANDEDNESS: single
(D) TOPOLOGY: linear (ii) MOLECULE TYPE: DNA (genomic)

(vi) ORIGINAL SOURCE:
    (B) STRAIN: Light chain variable region for monoclonal
        antibody 5B6

(ix) FEATURE:
    (A) NAME/KEY: CDS
    (B) LOCATION: 1..321

(xi) SEQUENCE DESCRIPTION: SEQ ID NO:25:

```
GAC ATC CAG ATG ACC CAG TCT CCA TCC TCC TTA TCT GCC TCT CTG GGA      48
Asp Ile Gln Met Thr Gln Ser Pro Ser Ser Leu Ser Ala Ser Leu Gly
 1               5                  10                  15

GAA AGA GTC ACT CTC ACT TGT CGG GCC AGT CAG GAC ATT GGT AGT AGT      96
Glu Arg Val Thr Leu Thr Cys Arg Ala Ser Gln Asp Ile Gly Ser Ser
                20                  25                  30

TTA AAC TGG CTT CAG CTG AAA CCA GAT GGA ACT ATT AAA CGC CTG ATC     144
Leu Asn Trp Leu Gln Leu Lys Pro Asp Gly Thr Ile Lys Arg Leu Ile
            35                  40                  45

TAC GCC ACA TCC GGT TTA GAT TCT GGT GTC CCC AAA AGG TTC AGT GGC     192
Tyr Ala Thr Ser Gly Leu Asp Ser Gly Val Pro Lys Arg Phe Ser Gly
 50                  55                  60

AGT AGG TCT GGG TCA GAT TAT TCT CTC ACC ATC AAC AGC CCT GAG TCT     240
Ser Arg Ser Gly Ser Asp Tyr Ser Leu Thr Ile Asn Ser Pro Glu Ser
 65                  70                  75                  80

GAA GAT TTT GTA GAC TAT TAC TGT CTA CAA TGT TCT AAT TCT CCG TAC     288
Glu Asp Phe Val Asp Tyr Tyr Cys Leu Gln Cys Ser Asn Ser Pro Tyr
                85                  90                  95

ACG TTC GGA GGG GGG ACC AAG CTG GAA ATA AAC                         321
Thr Phe Gly Gly Gly Thr Lys Leu Glu Ile Asn
                100                 105
```

(2) INFORMATION FOR SEQ ID NO:26:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:26:

```
Asp Ile Gln Met Thr Gln Ser Pro Ser Ser Leu Ser Ala Ser Leu Gly
 1               5                  10                  15

Glu Arg Val Thr Leu Thr Cys Arg Ala Ser Gln Asp Ile Gly Ser Ser
                20                  25                  30

Leu Asn Trp Leu Gln Leu Lys Pro Asp Gly Thr Ile Lys Arg Leu Ile
            35                  40                  45

Tyr Ala Thr Ser Gly Leu Asp Ser Gly Val Pro Lys Arg Phe Ser Gly
 50                  55                  60

Ser Arg Ser Gly Ser Asp Tyr Ser Leu Thr Ile Asn Ser Pro Glu Ser
 65                  70                  75                  80

Glu Asp Phe Val Asp Tyr Tyr Cys Leu Gln Cys Ser Asn Ser Pro Tyr
                85                  90                  95

Thr Phe Gly Gly Gly Thr Lys Leu Glu Ile Asn
                100                 105
```

(2) INFORMATION FOR SEQ ID NO:27:

(i) SEQUENCE CHARACTERISTICS:
           (A) LENGTH: 34 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
           (B) STRAIN: Primer 2034 used for cDNA synthesis and/or
               PCR amplification (xi) SEQUENCE DESCRIPTION: SEQ ID NO:27:

GCCAGTGATC AAGGGTTAGA CCAGATGGGG CTGT                                        34

(2) INFORMATION FOR SEQ ID NO:28:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
           (B) STRAIN: Primer 438 used for cDNA synthesis and/or
               PCR amplification (xi) SEQUENCE DESCRIPTION: SEQ ID NO:28:

GGCAGCACTA GTAGGGGCCA GCAGTGGATA                                             30

(2) INFORMATION FOR SEQ ID NO:29:

(i) SEQUENCE CHARACTERISTICS:
           (A) LENGTH: 39 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
           (B) STRAIN: Primer SS92

(xi) SEQUENCE DESCRIPTION: SEQ ID NO:29:

GGACTTCCGA GCTCGATGTT TTGATGACCC AAACTCCAC                                   39

(2) INFORMATION FOR SEQ ID NO:30:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
           (B) STRAIN: Primer 33615

(xi) SEQUENCE DESCRIPTION: SEQ ID NO:30:

GAAGATCTAG ACTTACTATG CAGCATCAGC                                             30

(2) INFORMATION FOR SEQ ID NO:31:

(i) SEQUENCE CHARACTERISTICS:
           (A) LENGTH: 39 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
            (B) STRAIN: Primer SS119

(xi) SEQUENCE DESCRIPTION: SEQ ID NO:31:

CCAGTTCCGA GCTCGACATG CAGATGACCC AGTCTCCAT                    39

(2) INFORMATION FOR SEQ ID NO:32:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (B) STRAIN: Strain SS131

(xi) SEQUENCE DESCRIPTION: SEQ ID NO:32:

AGGTCCAGCT GCTCGAGGTC CAGCTGCAGC AGT                          33

(2) INFORMATION FOR SEQ ID NO:33:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (B) STRAIN: Strain 65656

(xi) SEQUENCE DESCRIPTION: SEQ ID NO:33:

AGGAGACTAG TGGTTACTAA TTTGGGAAGG ACTG                         34

(2) INFORMATION FOR SEQ ID NO:34:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (B) STRAIN: Vha Primer (xi) SEQUENCE DESCRIPTION: SEQ ID NO:34:

AGGTCCAGCT GCTCGAGTCT GG                                      22

(2) INFORMATION FOR SEQ ID NO:35:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (B) STRAIN: VH primer (xi) SEQUENCE DESCRIPTION: SEQ ID NO:35:

AGGTCCAACT GCTCGAGTCT GG                                      22

(2) INFORMATION FOR SEQ ID NO:36:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

GAGACGACTA GTGGTGGCGG TGGCTCTCCA TTCGTTTGTG AATATCAA        48

(2) INFORMATION FOR SEQ ID NO:37:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

TTACTAGCTA GCATAATAAC GGAATACCCA AAAGAACTGG        40

(2) INFORMATION FOR SEQ ID NO:38:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

TATGCTAGCT AGTAACACGA CAGGTTTCCC GACTGG        36

(2) INFORMATION FOR SEQ ID NO:39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

AGCTTTGAAT TCGTGAAATT GTTATCCGCT        30

What is claimed is:

1. A metal binding polypeptide comprising a Fab fragment capable of binding to a mercury cation, wherein the Fab fragment includes an amino acid sequence for a heavy chain variable region from monoclonal antibody 4A10 (SEQ ID NO: 2, monoclonal antibody 1C11 (SEQ ID NO: 4), monoclonal antibody 5G4 (SEQ ID NO: 6), monoclonal antibody 23F8 (SEQ ID NO: 8), monoclonal antibody 2D5 (SEQ ID NO: 10), or monoclonal antibody 5B6 (SEQ ID NO: 12).

2. The polypeptide of claim 1 wherein the Fab fragment comprises an amino acid sequece for a light chain variable region from monoclonal antibody 1F10 (SEQ ID NO:14), monoclonal antibody 4A10 (SEQ ID NO:16), monoclonal antibody 1C11 (SEQ ID NO:18), monoclonal antibody 5G4 (SEQ ID NO:20), monoclonal antibody 23F8 (SEQ ID NO:22), monoclonal antibody 2D5 (SEQ ID NO:24) or monoclonal anbibody 5B6 (SEQ ID NO:26).

3. The polypeptide of claim 1 wherein said polypeptide is a recombinantly produced Fab fragment.

4. The polypeptide of claim 1 wherein said polypeptide comprises a Fab fragment which includes the amino acid sequence for the heavy chain variable region from monoclonal antibody 1C11 (SEQ ID NO: 4).

5. The polypeptide of claim 1 wherein said polypeptide comprises a Fab fragment which includes the amino acid sequence for the heavy chain variable region from monoclonal antibody 5G4 (SEQ ID NO: 6).

6. The polypeptide of claim 1 wherein said polypeptide comprises a Fab fragment which includes the amino acid sequence for the heavy chain variable region from monoclonal antibody 23F8 (SEQ ID NO: 8).

7. The polypeptide of claim 1 wherein said polypeptide comprises a Fab fragment which includes the amino acid sequence for the heavy chain variable region from monoclonal antibody 2D5 (SEQ ID NO: 10).

8. The polypeptide of claim 1 wherein said polypeptide comprises a Fab fragment which includes the amino acid sequence for the heavy chain variable region from monoclonal antibody 5B6 (SEQ ID NO: 12).

9. The polypeptide of claim 1 wherein said polypeptide comprises a heavy chain Fc fragment fused to a heavy chain Fd fragment which includes the light chain variable region amino acid sequence.

10. The polypeptide of claim 1 wherein said polypeptide comprises a phage coat protein or portion thereof fused to the heavy chain Fd fragment which includes the light chain variable region amino acid sequence.

11. The polypeptide of claim 3 wherein the Fab fragment comprises an amino acid sequence for a light chain variable region from monoclonal antibody 1F10 (SEQ ID NO: 14) or monoclonal antibody 4A10 (SEQ ID NO: 16).

12. The polypeptide of claim 1 wherein the Fab fragment comprises a heavy chain Fd fragment; and further comprising an amino acid sequence that functions to direct the heavy chain Fd fragment to a membrane in a host.

13. The polypeptide of claim 1 wherein the Fab fragment comprises a heavy chain variable region amino acid sequence from a first monoclonal antibody and the light chain variable region amino acid sequence from a second monoclonal antibody.

14. The polypeptide of claim 13 wherein the second monoclonal antibody does not bind to the mercury cation.

15. The polypeptide of claim 1 wherein the mercury cation is a mercuric cation.

16. A kit for detecting the presence of mercury cations comprising a metal binding polypeptide which includes a Fab fragment capable of binding to a mercury cation, wherein the Fab fragment includes an amino acid sequence for a heavy chain variable region from monoclonal antibody 4A10 (SEQ ID NO:2), monoclonal antibody 1C11 (SEQ ID NO: 4), monoclonal antibody 5G4 (SEQ ID NO: 6), monoclonal antibody 23F8 (SEQ ID NO: 8), monoclonal antibody 2D5 (SEQ ID NO:10), monoclonal antibody 5B6 (SEQ ID NO: 12).

17. The kit of claim 46 wherein said polypeptide comprises a Fab fragment which includes the amino acid sequence for the heavy chain variable region from a monoclonal antibody selected from the group consisting of monoclonal antibody 1C11, monoclonal antibody 5G4, monoclonal antibody 23F8, monoclonal antibody 2D5, or monoclonal antibody 5B6.

18. The kit of claim 16 wherein the Fab fragment comprises an amino acid sequence for a light chain variable region from monoclonal antibody 1F10 (SEQ ID NO:14), monoclonal antibody 4A10 (SEQ ID NO:16), monoclonal antibody 1C11 (SEQ ID NO:18), monoclonal antibody 5G4 (SEQ ID NO:20), monoclonal antibody 23F8 (SEQ ID NO:22), monoclonal antibody 2D5 (SEQ ID NO:24) or monoclonal antibody 5B6 (SEQ ID) NO:26).

19. The kit of claim 16 wherein the mercury cation is a mercuric cation.

20. The kit of claim 16 wherein the Fab fragment comprises a heavy chain variable region amino acid sequence from a first monoclonal antibody and the light chain variable region amino acid sequence from a second monoclonal antibody.

21. The polypeptide of claim 1 wherein said polypeptide comprises a Fab fragment which includes the amino acid sequence for the heavy chain variable region from monoclonal antibody A410 (SEQ ID NO: 2).

22. The polypeptide of claim 1 wherein said polypeptide is monoclonal antibody A410 produced by hybridoma cell line ATCC No. HB10381.

* * * * *